US012597514B2

(12) United States Patent    (10) Patent No.:   US 12,597,514 B2

Räisänen     (45) Date of Patent:     Apr. 7, 2026

(54) WEARABLE SENSOR AND SYSTEM THEREOF

(71) Applicant: Emfit Ltd., Vaajakoski (FI)

(72) Inventor: Heikki Räisänen, Muurame (FI)

(73) Assignee: Emfit Ltd., Vaajakoski (FI)

( * ) Notice: Subject to any disclaimer, the term of this patent is extended or adjusted under 35 U.S.C. 154(b) by 0 days.

(21) Appl. No.: 18/651,557

(22) Filed: Apr. 30, 2024

(65) Prior Publication Data

US 2025/0104855 A1     Mar. 27, 2025

Related U.S. Application Data

(63) Continuation of application No. 16/605,110, filed as application No. PCT/US2018/027728 on Apr. 16, 2018, now Pat. No. 11,972,863.

(60) Provisional application No. 62/613,034, filed on Jan. 2, 2018, provisional application No. 62/612,301, filed on Dec. 29, 2017, provisional application No. 62/575,517, filed on Oct. 22, 2017, provisional application No. 62/525,723, filed on Jun. 27, 2017, provisional application No. 62/485,648, filed on Apr. 14, 2017.

(51) Int. Cl.
| | |
|---|---|
| *A61B 5/00* | (2006.01) |
| *A61B 5/0205* | (2006.01) |
| *A61B 5/318* | (2021.01) |
| *G06F 1/26* | (2006.01) |
| *G16H 40/63* | (2018.01) |

(52) U.S. Cl.
CPC .............. *G16H 40/63* (2018.01); *A61B 5/00* (2013.01); *A61B 5/0205* (2013.01); *A61B 5/318* (2021.01); *A61B 5/4815* (2013.01);

*A61B 5/6892* (2013.01); *G06F 1/26* (2013.01); *A61B 2560/0204* (2013.01); *A61B 2560/0443* (2013.01)

(58) Field of Classification Search
None
See application file for complete search history.

(56) References Cited

U.S. PATENT DOCUMENTS

| | | | | |
|---|---|---|---|---|
| 11,972,863 B2 * | 4/2024 | Räisänen | ............. | A61B 5/4818 |
| 2007/0106183 A1 * | 5/2007 | Suzuki | ................. | A61B 5/4812 |
| | | | | 600/595 |
| 2007/0112283 A1 * | 5/2007 | Ando | ..................... | A61B 5/103 |
| | | | | 600/587 |
| 2007/0205701 A1 * | 9/2007 | Grumm | ................ | A61B 5/4818 |
| | | | | 310/800 |
| 2009/0312612 A1 * | 12/2009 | Rantala | ................ | A61B 5/0205 |
| | | | | 702/19 |

(Continued)

FOREIGN PATENT DOCUMENTS

| | | | | |
|---|---|---|---|---|
| WO | WO-2008096307 A1 * | 8/2008 | ........... | A61B 5/0002 |

*Primary Examiner* — Shirley X Jian

(74) *Attorney, Agent, or Firm* — Hassan Abbas Shakir; Shakir Law PLLC

(57) ABSTRACT

A system for monitoring quantitative health data of a user, the system includes a stationary sensor device for monitoring a first set of quantitative health data of the user when the user is resting in bed; and a wearable tracker for monitoring a second set of quantitative health data of the user when the user is resting; wherein the wearable tracker is worn by the user; the first set and second set are sequential in time to obtain around-the-clock monitoring of the quantitative health data of the user.

19 Claims, 16 Drawing Sheets

(56)  References Cited

U.S. PATENT DOCUMENTS

| | | | |
|---|---|---|---|
| 2010/0056872 A1* | 3/2010 | Kahn ................... | A61B 5/1112 |
| | | | 600/300 |
| 2014/0335490 A1* | 11/2014 | Baarman .............. | A61B 5/1118 |
| | | | 434/236 |
| 2016/0015315 A1* | 1/2016 | Auphan .............. | A61B 5/7435 |
| | | | 600/587 |
| 2017/0049367 A1* | 2/2017 | Moore ................ | A61B 5/4806 |
| 2017/0358942 A1* | 12/2017 | Pugh ..................... | A61B 5/021 |

* cited by examiner

WEARABLE SENSOR AND SYSTEM THEREOF

CROSS-REFERENCE TO RELATED APPLICATIONS

This application is a continuation application of and claims priority from U.S. Ser. No. 16/605,110, which was filed Oct. 14, 2019 which is pending and which is hereby incorporated by reference in its entirety for all purposes.

U.S. Ser. No. 16/605,110 is a National Stage Entry of and claims priority from PCT/US2018/027728, which was filed Apr. 16, 2018 and has been published, and which is hereby incorporated by reference in its entirety for all purposes.

Application PCT/US2018/027728 claims priority from provisional application U.S. Ser. No. 62/485,648, which was filed Apr. 14, 2017 and is now expired, and which is hereby incorporated by reference in its entirety for all purposes.

Application PCT/US2018/027728 claims priority from provisional application U.S. Ser. No. 62/525,723, which was filed Jun. 27, 2017 and is now expired, and which is hereby incorporated by reference in its entirety for all purposes.

Application PCT/US2018/027728 claims priority from provisional application U.S. Ser. No. 62/575,517, which was filed Oct. 22, 2017 and is now expired, and which is hereby incorporated by reference in its entirety for all purposes.

Application PCT/US2018/027728 claims priority from a provisional application U.S. Ser. No. 62/612,301, which was filed Dec. 29, 2017 and is now expired, and which is hereby incorporated by reference in its entirety for all purposes.

Application PCT/US2018/027728 claims priority from a provisional application U.S. Ser. No. 62/613,034, which was filed Jan. 2, 2018 and is now expired, and which is hereby incorporated by reference in its entirety for all purposes.

BACKGROUND OF THE INVENTION

Field of the Invention

The invention relates to a sensor disposed to record one or more quantitative health data continuous over time from a human or animal and a system thereto. More specifically, the invention is directed to a wearable tracker 102b incorporating a sensor for recording one or more quantitative health data continuous during sleeping hours of a subject as well as a sensor for recording one or more quantitative health data continuous during waking hours of the subject.

Discussion of the Related Art

A person seeking insight (hereinafter "a user") into their own or another person's sleeping patterns (also, "a subject" or "a patient") may use an electrical device, electromechanical device, or software running on a monitoring device for tracking the subject's sleep. "Tracking" is used in the art (and is used in this manner in the present application) to mean acquiring quantitative health data of the user's sleep and/or determining qualitative health data of the user's sleep.

One aspect of health is sleep. Sleep is an important factor in human health and its value is being increasingly more recognized and valued. Unfortunately, certain medical conditions adversely affect sleep. Sleep apnea (central and/or obstructive) is an illness that affects many people and has different causes. Heart arrhythmias are of many different types and impair effective, restful sleep. While the preferred method for determining arrhythmias requires using electrocardiograms that are expensive and time-consuming to administer to a patient, most arrhythmias can be diagnosed, in fact, using ballistocardiography.

Many kinds of sleep trackers are available on the market using different technologies to acquire a quantitative health data. Most sleep trackers are based on measuring ballistocardiography of forces exerted by the heart, lungs, and body movements. Sleep trackers using ballistocardiography typically measure changes in the air pressure from an air pressure sensor installed into an air chamber provided in the mattress on which the subject sleeps. This concept used by the Sleep IQ USA. Other sleep trackers are based on radar waves, for example, the ResMed S+non-contact sleep sensor. Accelerometer based sleep trackers are also on the market from, for example, Murata. However, most sleep trackers appear to be based on piezoelectric materials like PZT or PVDF.

One sleep tracker based on ballistocardiographic principle is the applicant's Emfit QS, which uses a cellular ferroelectret and permanently charged material in between two electrodes and generates charge proportional to forces applied onto it. Other sleep trackers come, for example, from manufacturers like Beddit, Sleepace, or EightSleep. Usually, these sleep trackers use one or more sensors and/or small electronic devices that are placed or installed onto, into, or under a mattress and communicate wirelessly using Bluetooth technology to send measured ballistocardiography sensor signal to a nearby smartphone for further calculating it into meaningful information of heart rate, perhaps heart rate variability, breathing rate, movement activity and generating often also qualitative health data and even some sleep disorders (sleep apnea, central and/or obstructive) information from the signal (for example, Beddit). In most cases, an application installed on a smartphone performs the band pass filtering, one or more signal acquisitions, and calculation to obtain the qualitative health data. However, these functions may be performed by a server sending data or sampled sensor signal over the internet.

Often the sleep tracker is a phone application or embedded device that sends the data to cloud for a user to access it with other devices using a browser. Some products, for example, the applicant's Emfit QS, have embedded calculation functions and perform most of the calculation in the application and send already calculated data, send also band-pass-filtered raw signal to server for a user's access via an internet browser. Further data analysis may be performed using a band-pass filter in order to filter signals. Therein, a physician may readily diagnose a variety of sleep disorders including obstructive sleep apnea or heart arrhythmias.

Also, application programming interfaces (API) are often used to send data to data integrators, for example, Validic or TraininPeaks. Embedded devices can deliver data to server, for example, using Wi-Fi or 3G/LTE technologies.

Many of the sleep trackers may also be used or be adapted for use in hospitals for contact-free vital signs (heart and breathing rate) monitoring of patient deterioration or detecting possible heart arrhythmias and diagnosing sleep apneas. Some manufacturers have separate hospital and home use versions, for example, EarlySense.

In contrast, activity trackers such as Fitbit or Garmin measure heart rate and a smart watches like Apple Watch perform many other feature including heart rate and step counting and have the ability to combine these with GPS. When a 3D accelerometer is also included in the device, the device can also differentiate walking from running, or even cycling and swimming.

There are also chest or body installed medical devices with an adhesive or a strap ECG based sensor system for measuring heart rate, heart rate variability, breathing rate, body temperature. Also, SpO$_2$ metering technology has been used on chest. Often these chest installed devices have Bluetooth or else wireless transceiver for data transmission.

At the present time, there is a significant and important need for out-patient monitoring of one or more physical conditions—for example, monitoring at home after for example, some more serious surgery. Often, deteriorating conditions of a patient may go unnoticed and re-admitting a patient to a hospital in bad condition soon after sending home is very expensive for hospital and society and uncomfortable for patient. These medical needs are addressed in media and many publications, for example, it is thoroughly discussed in European Union project Nightingale.

However, an important and unmet need is that a complete system for easy, safe, robust, and accurate remote around-the-clock monitoring of vital signs is not available. For reasons of comfort, users do not wish to use anything on their body at night nor on their wrist or chest. During the day, users can easily accept wrist device, pendants on their neck, and even chest strap but even on wearable tracker 102b with adhesive instalment is often uncomfortable. This is especially so, when need is to continue monitoring for months and even years, as can be with people with heart arrhythmias. Usability is the greatest importance for creating long term sustained traction between users and a device; therein, the most important aspect for a user is easy daily use. Easy daily use preferably means that device is used for its intended purpose at daytime and is being charged at night when the user is sleeping. Therein, charging station or dock of the sensor 100b in daytime wearable tracker 102b device should be closest to bed. Advantageously, by having the docking station or charger close to bed makes the idea of charging the last step before going to sleep. In the morning, the device is readily available while still is sitting on the bed. In the present invention, the usability problems are being solved.

Also, complying whole system from many different technologies, for example, ECG and SpO$_2$, causes complexity in signal analysis which can easily cause high rate of false alarms to monitoring central. False alarms create high barrier for user adoption of the product. As important as high sensitivity is needed for alerts, is high specificity to minimize false alarms. Also actual cost is great importance. Product for outpatient around-the-clock monitoring should be low cost as numbers of outpatients are very large.

SUMMARY OF THE INVENTION

A system for monitoring quantitative health data of a user, the system includes a stationary sensor device for monitoring a first set of quantitative health data of the user when the user is resting in bed; and a wearable tracker for monitoring a second set of quantitative health data of the user when the user is resting; wherein the wearable tracker is worn by the user; the first set and second set are sequential in time to obtain around-the-clock monitoring of the quantitative health data of the user.

The system further comprises a system manager comprising a computing device for acquiring the first set of the quantitative health data of the user from the stationary sensor device.

The system includes a wearable tracker that comprises a rechargeable power source, the system manager comprises a charger for charging the rechargeable power source.

The system includes n the charger is an inductive charger.

The stationary sensor device comprises a first sensor and the wearable tracker comprises a second sensor, the first sensor and the second sensor comprising different sensor types.

The first sensor comprises a ferroelectret film and the second sensor comprises microelectromechanical system.

The computing device acquires the second set of the quantitative health data of the user from the wearable tracker.

The system includes a first system manager comprising a first computing device for acquiring the quantitative health data of the user from the stationary sensor;

a second system manager comprising a second computing device for acquiring quantitative health data of the user from the stationary sensor.

The stationary sensor device comprises a sensor, the sensor comprises a ferroelectret film having an active sensor section and an inactive sensor section, the active sensor section placed proximate to the user and the inactive sensor section being proximate to an interference source.

The active sensor section comprises a plurality of ferroelectret film layers for increased sensitivity.

The system includes a webbed tubing, wherein the active sensor section is disposed in the webbed tubing to protect from damage.

The wearable tracker is selected from a smartphone, a watch, or a chest-worn device.

BRIEF DESCRIPTION OF THE INVENTION

The drawings illustrate one or more embodiments of the present invention.

5

Figures 9A, 9B, 10C:
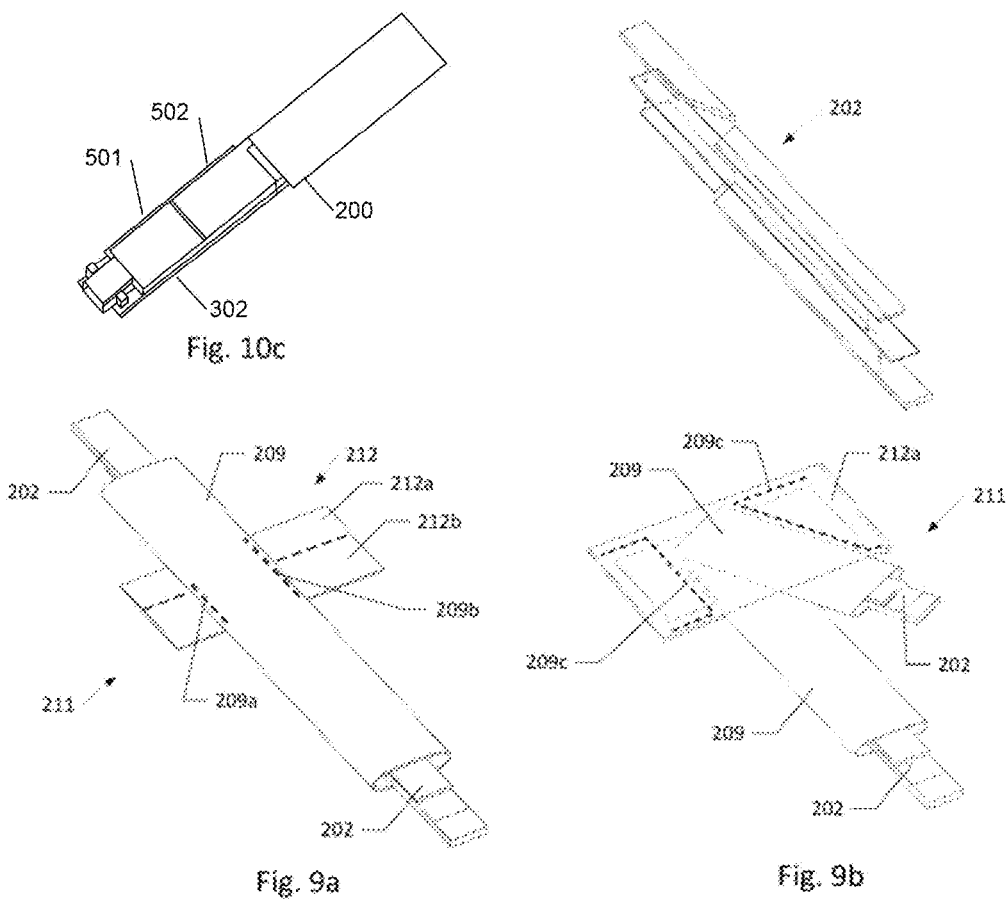
FIGS. 9a and 9b are schematic diagrams of a construction method of a portion of a stationary sensor in accordance with one or more embodiments of the present invention.
Figure 10A:
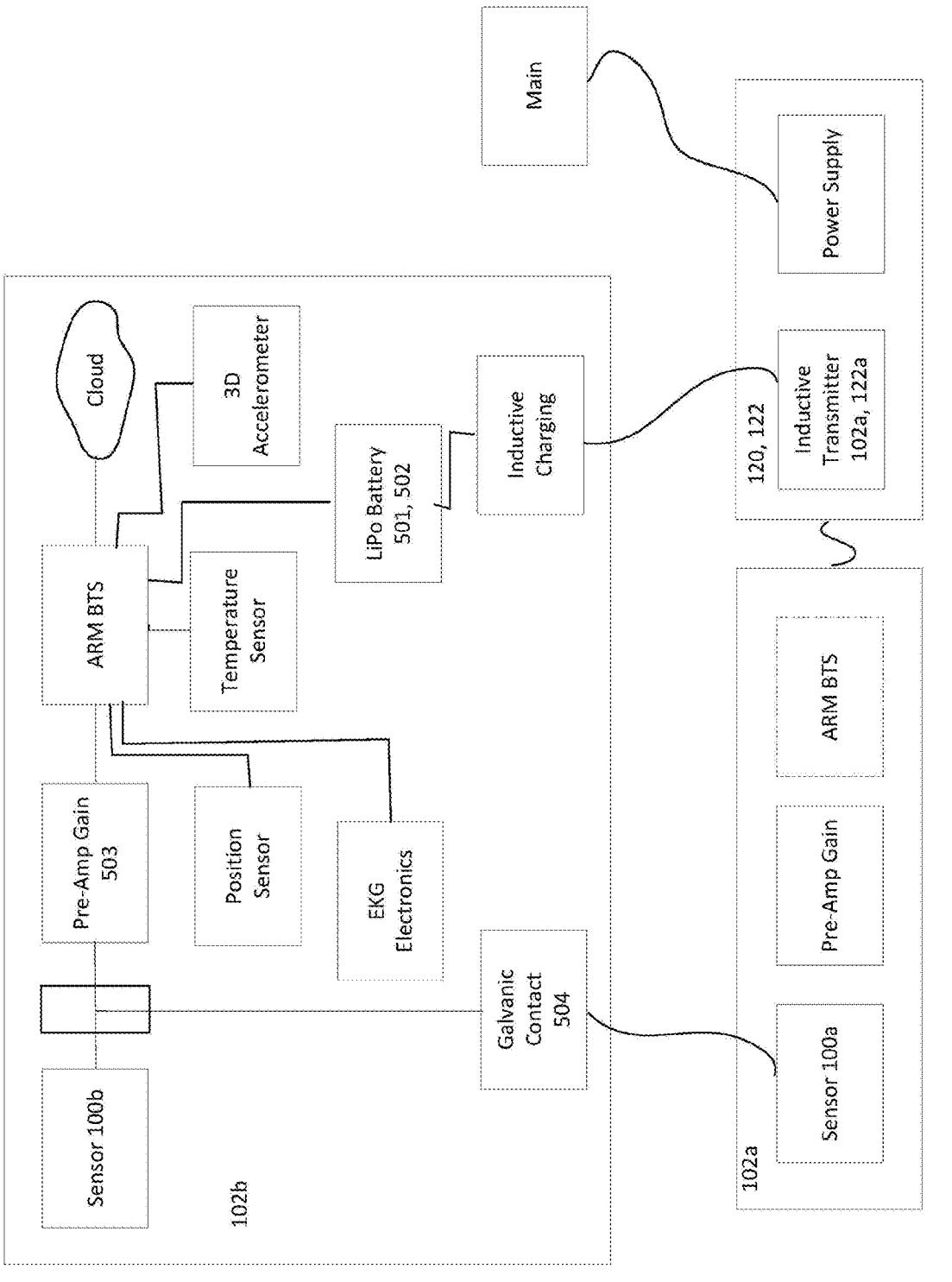

FIG. 10*a* is a schematic diagram of a stationary sensor, a wearable tracker, and one or more system managers in accordance with one or more embodiments of the present invention.

Figure 10B:
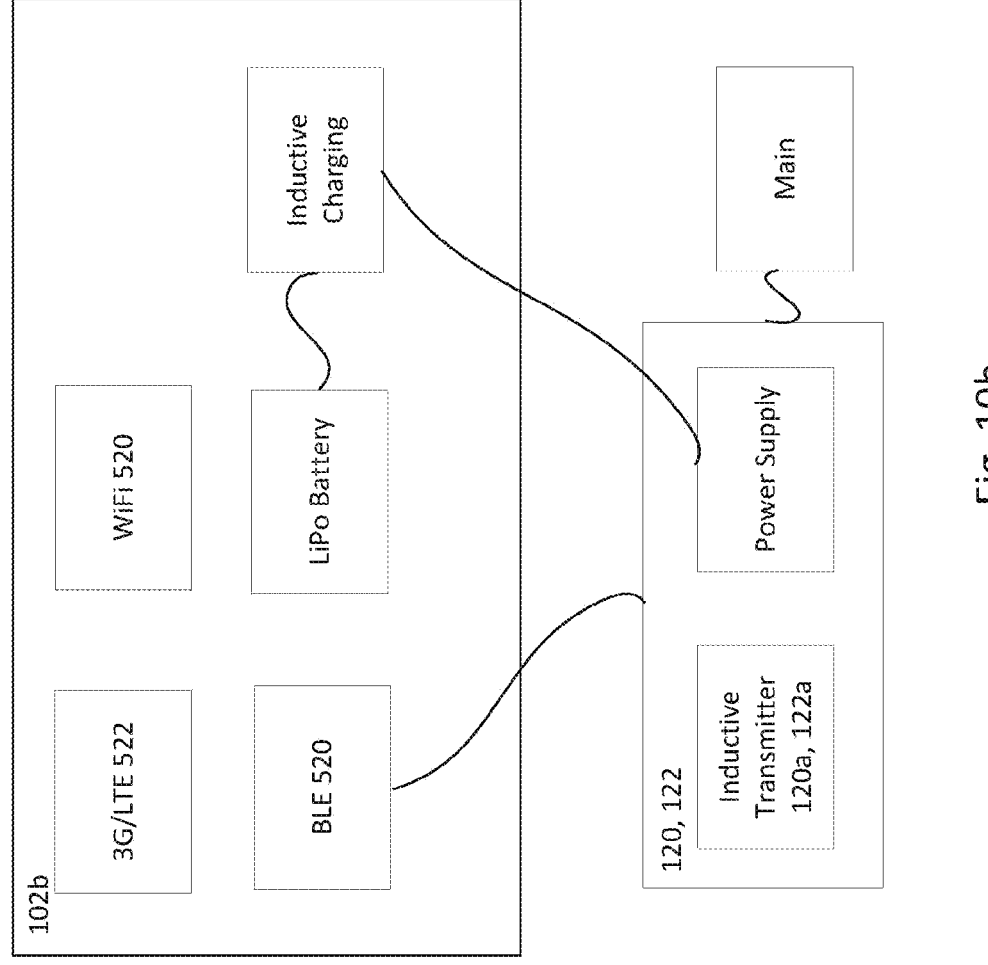

FIG. 10*b* is a schematic diagram of a wearable tracker and one or more system managers in accordance with one or more embodiments of the present invention.

FIG. 10*c* is a schematic diagram of a portion of a stationary sensor in accordance with one or more embodiments of the present invention.

Figures 11A, 11B, 11C:
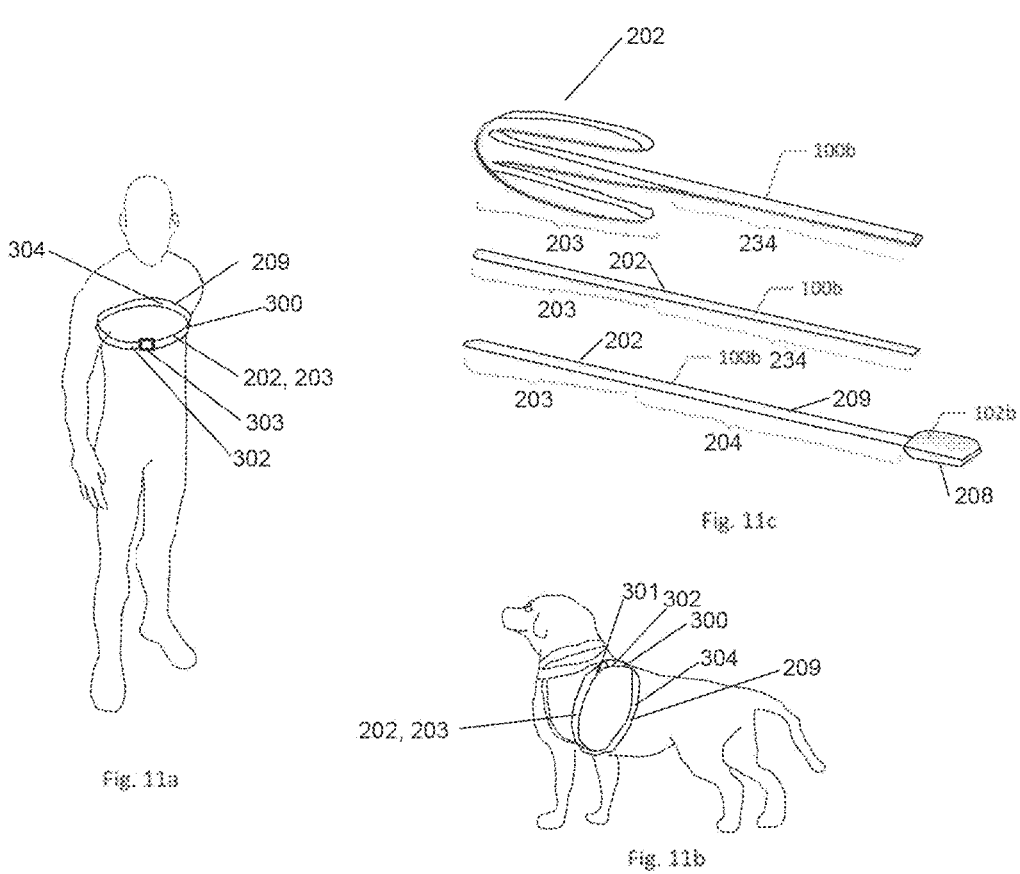

FIGS. 11*a* and 11*b* are schematic diagrams of a wearable tracker and sensor on a user in accordance with one or more embodiments of the present invention.

Figure 11D:
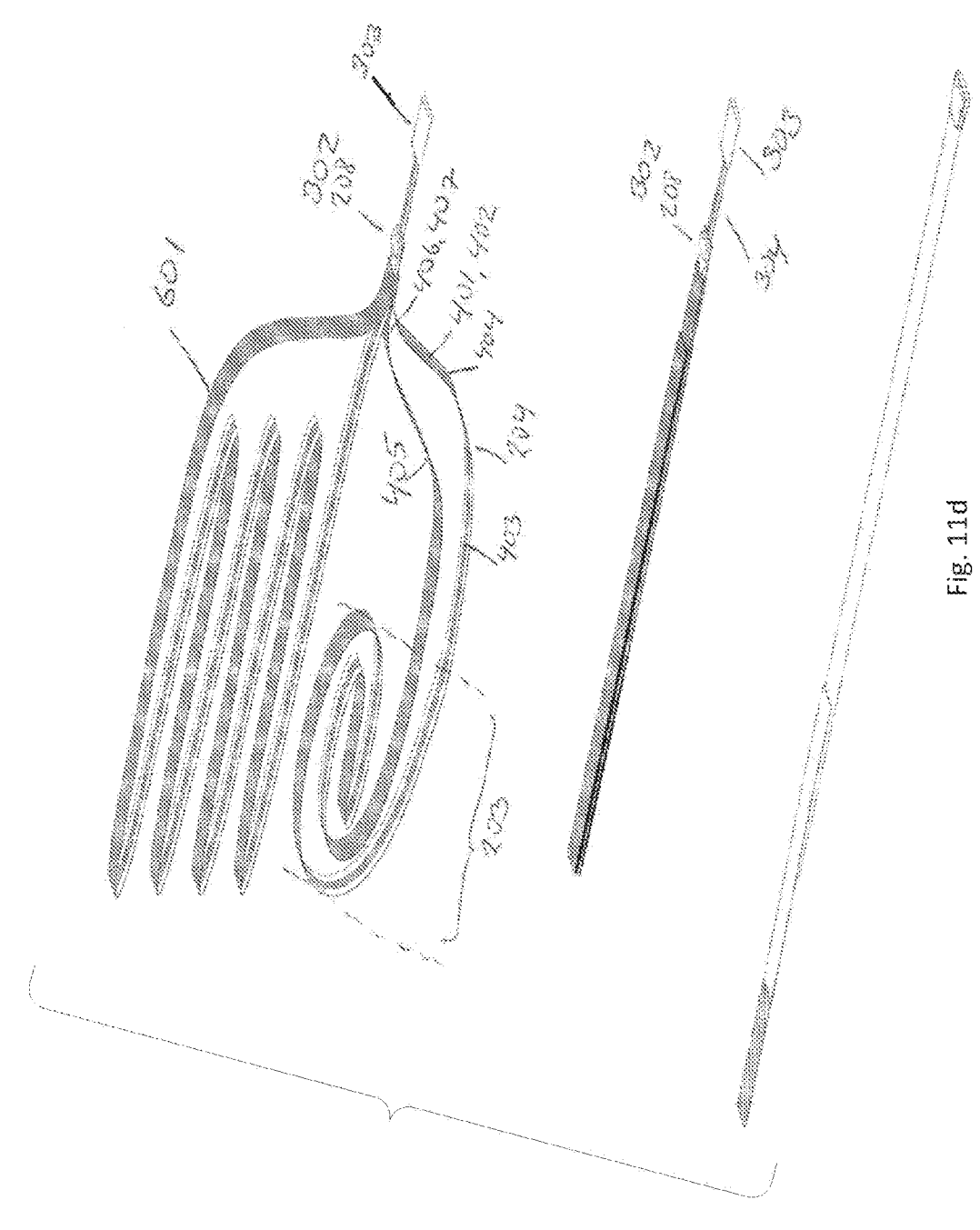

FIGS. 11*c* and 11*d* are schematic diagrams of a construction of a stationary sensor in accordance with one or more embodiments of the present invention.

Figure 12A:
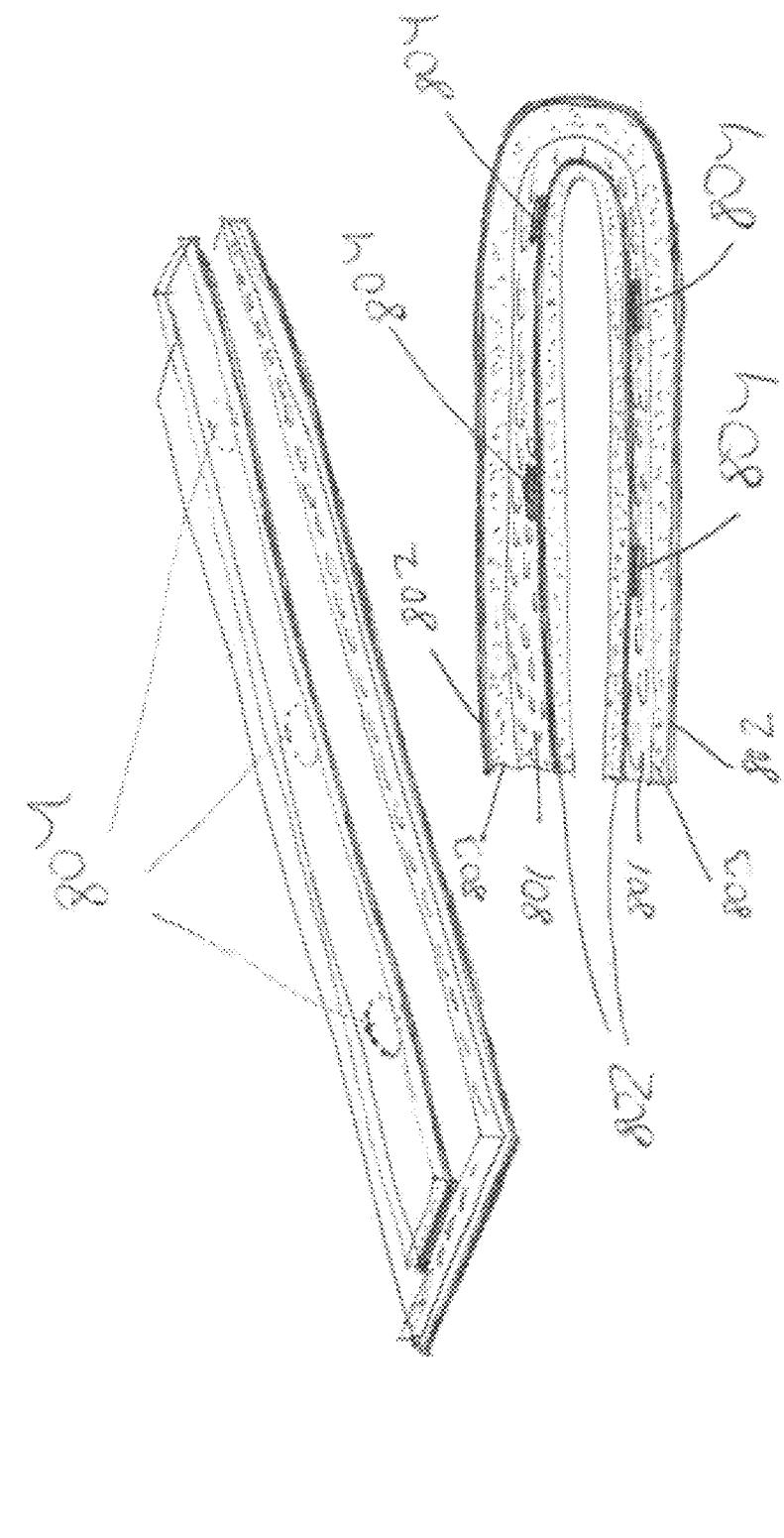
Figure 12:
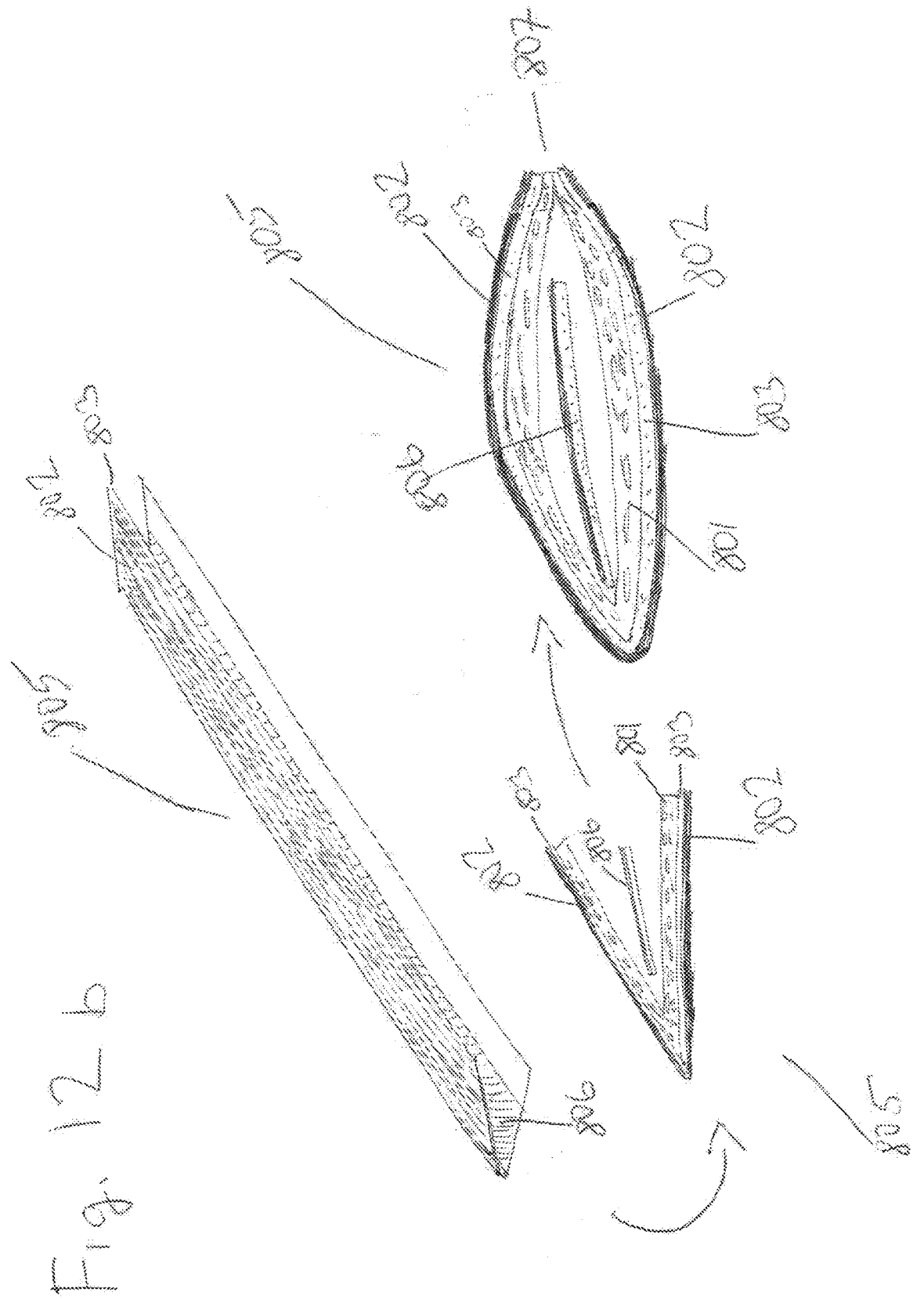

FIGS. 12*a* and 12*b* shows schematic diagrams of a ribbon type BCG sensor.

DETAILED DESCRIPTION OF THE INVENTION

Although, the embodiments that are discussed are relative to a human patient in a hospital and home setting the application is not limited narrowly to such settings. For example, all of the embodiments may be used with regard to one or more animals who are the patient. One example is hospital out-patient monitoring when they return home after a surgical procedure. In accordance with one or more embodiments of the present invention, the present invention may be used before that while patient stays in a hospital before going home.

Definitions

All technical and scientific terms shall have the same meaning as commonly understood by one of ordinary skill in the art. Nonetheless, the following terms are defined below to aid in the understanding of the disclosure and the definitions apply to all parts of speech of the term regardless whether the term is defined explicitly as such.

"About," "approximately," or "substantially similar" refer to a 10% variation from the nominal value. Even if not explicitly stated, it is understood that a variation is always included in a given value, whether or not the variation is specifically referenced.

Herein, "hospital" may also, besides its plain meaning, mean ambulatory surgical centers, nursing home, convalescence home, or any other facility offering treatment for medical, psychological, addiction, behavioral issues, or any other treatment options now know or to be devised where professionals are readily and/or immediately available in person or via a communications device to a patient to render or effect assistance.

Herein, "home" may also, besides its plain meaning, mean any other location besides "hospital" where professionals are less readily and/or immediately available than in hospital in person or via a communications device to a patient to render or effect assistance.

Herein, "a user" seeks insight into his/her own or another person's health ("a subject" or "a patient") may use an electrical device, electromechanical device, or software running on a device (hereinafter "a tracker") for tracking the quantitative health data of the subject.

"Tracking" means acquiring quantitative health data of the subject and/or determining qualitative health data of the subject.

Herein, a "patient" or preferably "subject" herein may be one or more human patients but may also be one or more veterinary patients, i.e., animals such as race horses. A "subject" may be but is not necessarily synonymous with a "user" and vice versa. Indeed, "user" may refer in the singular to one or more persons and/or entities, such as a patient, a subject, and a hospital organization in combination. However, for simplicity and general readability of this application, user and subject are interchangeably used. It should be appreciated that the reader should consider the user and subject are not interchangeable as well as that they are interchangeable.

Herein, "quantitative health data" (QN) of one or more subjects preferably is/are:

(i) one or more time measurements (for example, as measured in seconds, minutes, or hours) of movement activity, heart rate, heart rate variability, breathing rate, movement activity, length of sleep, periods of wakefulness, and the like at an absolute value, at or above a relative value compared to another predetermined value, at or above a predetermined or dynamic threshold value, at or above a predetermined or dynamic relative change;

(ii) one or more quantitative measurements, in any suitable and/or convenient unit of measure now known or to be devised, of heart rate (for example, in beats per second), the patient's heart rate variability (difference in milliseconds between heart beats (for example, measured via electrocardiography)), breathing rate, movement activity, and the like; and/or (iii) any other data that can be measured objectively (for example, blood oxygen saturation levels).

Herein, "qualitative health data" (QL) of one or more subjects are objective and/or subjective analysis, judgment, graphing, and/or any other data manipulation of:

(i) one or more quantitative health data exceed or fall below one or more (1) relative value compared to another predetermined value, (2) predetermined or dynamic threshold value, and/or (3) predetermined or dynamic relative change;

(ii) one or more quantitative health data of a first user relative to one or more quantitative health data of the first user, another user, a group of users, and/or one or more normative groups, guides, guidelines, and/or determinations by one or more professionals; and/or (iii) one or more qualitative health data of a first user relative to one or more qualitative health data of the first user, another user, a group of users, and/or one or more normative groups, guides, guidelines, and/or determinations by one or more professionals.

Forms of the verb "to capture" or "to record" mean to (a) acquire quantitative health data through one or more sensors and/or (b) save that quantitative health data to one or more files having any suitable format to any suitable non-transitory computer-readable memory.

"Computing device," or interchangeably "hardware," is intended in this disclosure for all purposes to be interpreted broadly and is defined for all uses, all devices, and/or all systems and/or systems in this disclosure as a device comprising at least a central processing unit, a communications device for interfacing with a data network, transitory computer-readable memory, and/or a non-transitory computer-readable memory and/or media. The central processing unit carries out the instructions of one or more computer programs stored in the non-transitory computer-readable memory and/or media by performing arithmetical, logical, and input/output operations to accomplish in whole or in part one or more steps of any method described herein. A computing device may have an onboard power source, access power from a draw power using a rechargeable battery or wall adapter (???).

A computing device is usable by one or more users, other computing devices directly and/or indirectly, actively and/or passively for one or more suitable functions herein. The computing device may be embodied as computer, a laptop, a tablet computer, a smartphone, camera, imaging device, and/or any other suitable device and may be a networked computing device, a server, or the like. Where beneficial, a computing device preferably includes one or more human input devices such as a computer mouse and/or keyboard and one or more human interaction device such as one or more monitors. A computing device may refer to any input, output, and/or calculating device associated with providing a virtual reality experience to one or more users.

Although one computing device may be shown and/or described, multiple computing devices may be used. Conversely, where multiple computing devices are shown and/or described, a single computing device may be used.

"Computer program," or interchangeably "software," means any set of instructions stored in a non-transitory computer-readable memory or non-transitory computer-readable media for executing one or more suitable functions and/or for executing one or more methods in this disclosure. Even if not explicitly mentioned, in this disclosure, a computing device includes software having any set of instructions stored in non-transitory computer-readable memory or non-transitory computer-readable media for executing one or more suitable functions and/or for executing one or more methods in this disclosure.

"Non-transitory computer-readable memory," or interchangeably "non-transitory computer-readable media," may be a hard drive, solid-state drive, compact disk drive, DVD drive, and/or the like for storing the one or more computer programs.

"Sensor" means the devices defined herein, but may also mean, to the extent usable with the present invention, a transducer used for converting one or more mechanical movements to electrical analog signals corresponding to the mechanical movements and encompasses all types of transducers.

"Device" shall beyond its common meaning also mean an item that protects one or more other units, such a sensor, retained within a housing comprising one or more parts, one or more ports to access the unit retained within the housing, and one or more buttons to control the unit retained within the housing.

Health Data System

Referring to FIGS. 1-6, in accordance with one or more embodiments of the present invention, a health data system 10 includes one or more sensors 100a, 100b disposed to record quantitative health data continuously over time from a human or animal subject (shown here generally as user 5).

In accordance with one or more embodiments of the present invention, a stationary sensor device 102a is disposed in or around the bed of user 5 and comprises a sensor 100a. Sensor 100a is disposed for recording contactlessly quantitative health data continuous around-the-clock during sleeping or resting hours of the user. User 5 preferably during waking hours wears a wearable health data tracker 102b. Wearable tracker 102b comprises a sensor 100b for recording quantitative health data continuous during waking hours of the user and preferably includes one or more computing devices for processing quantitative health data from sensor 100b.

The advantageous usability of the health data system 10 is achieved by having preferably two similar technology based sensors 100a, 100b that work together for continuous around-the-clock use. For example, piezoelectric, ferroelectret quasi-piezoelectric, or microelectromechanical systems (MEMS) are used in combination.

Sensor 100a uses a ferroelectret film, such as the Emfit sensor available from Emfit Oy of Finland. Sensor 100a is installed under a bed mattress or mattress topper 82 of bed 80 where the user sleeps and/or rests, preferably, with regularity. Stationary sensor device 102a is preferably configured to be suitable electronic device wherein sensor 100a is connected via a durable communications and/or power cable 103a for signal acquisition to system manager 120 on the floor nearby bed 80.

System manager 120 is a device comprising a computing device used for acquiring quantitative health data signals from sensor 100a and a charging device for charging a power source such as a battery for portable sensor 100b incorporated in wearable tracker 102b.

Figure 1:
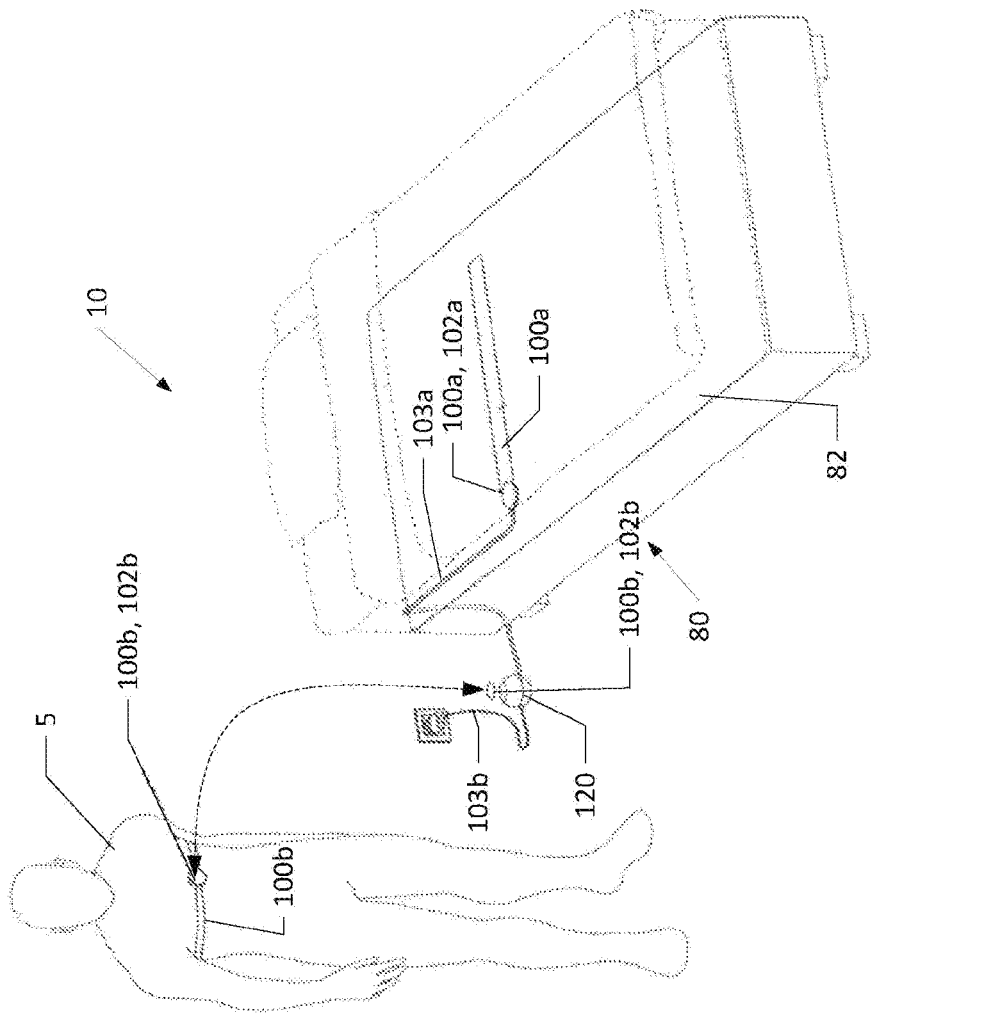
FIG. 1 is a schematic diagram of a health data system that includes one or more sensors disposed to record quantitative health data continuously over time in accordance with one or more embodiments of the present invention.
Figure 2:
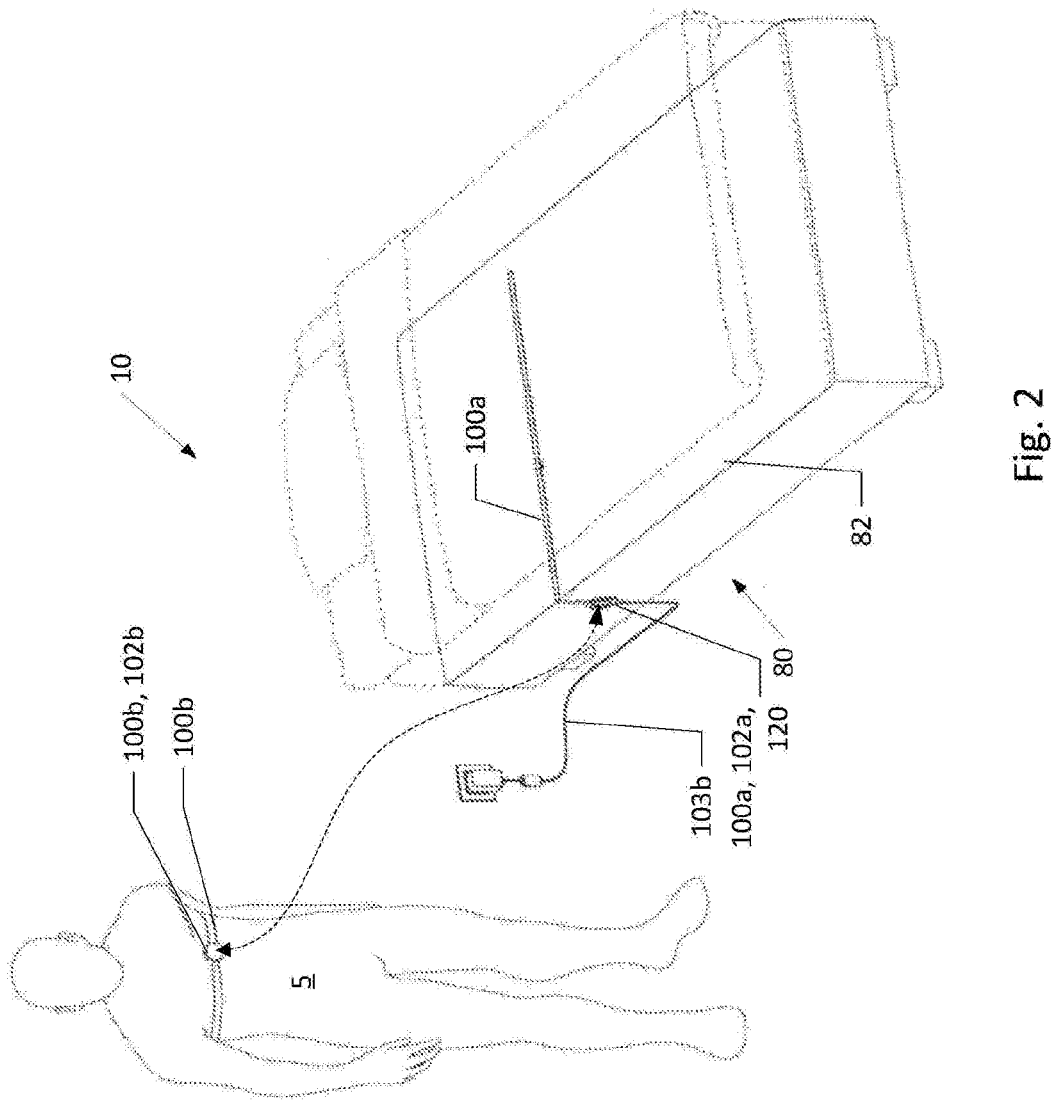
FIG. 2 is a schematic diagram of a health data system that includes one or more sensors disposed to record quantitative health data continuously over time in accordance with one or more embodiments of the present invention.

As shown in FIG. 2, system manager 120 may be disposed from a bed end, which advantageously eliminates the need for cable 103a, leaving only power cable 103b.

Figure 3:
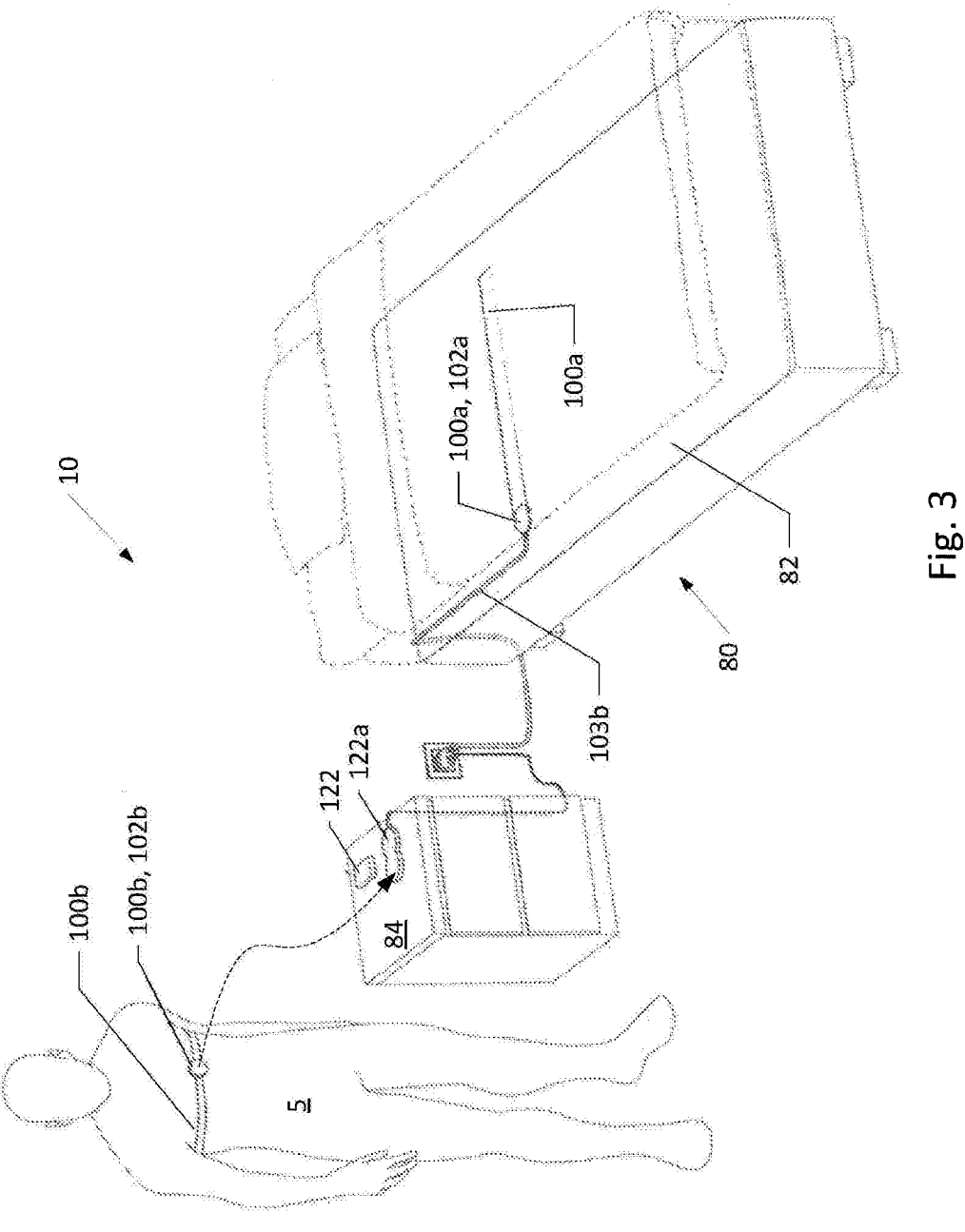
FIG. 3 is a schematic diagram of a health data system that includes one or more sensors disposed to record quantitative health data continuously over time in accordance with one or more embodiments of the present invention.

As shown in FIG. 3, a system manager 122 is similar to system manager 120 and may be placed on a table 84 near the user when sleeping. System manager 122 is preferably used for charging wearable tracker 102b and as a system manager for acquiring signals from sensor 100b.

Preferably, each system manager 120, 122 or at least one system manager 120, 122 comprises a charging coil 122a or charging coil 122a is separate from system manager 122. Charging coil 122a is, for example, inductive charging such that wearable tracker 102b is ready for daytime use by the user while away from bed 80. Wearable tracker 102b may be any suitable portable form but preferably is a chest sensor worn on the user's chest and/or utilizes small ballistocardiography as used in sensor 100a. System manager 122 may be a smartphone and is connectable to wearable tracker 102b through a wireless connection.

When the user leaves bed 80 in the morning, the user removes wearable tracker 102b from the takes portable sensor 100b in wearable tracker 102b with himself/herself and can hang sensor 100b in tracker 102b on his/her neck or slip on a chest strap 103c or into a small pocket on a shirt placed against area of heart. During the night, wearable tracker 102b and/or sensor 100b are charged for daytime use by system manager 120.

Figure 4:
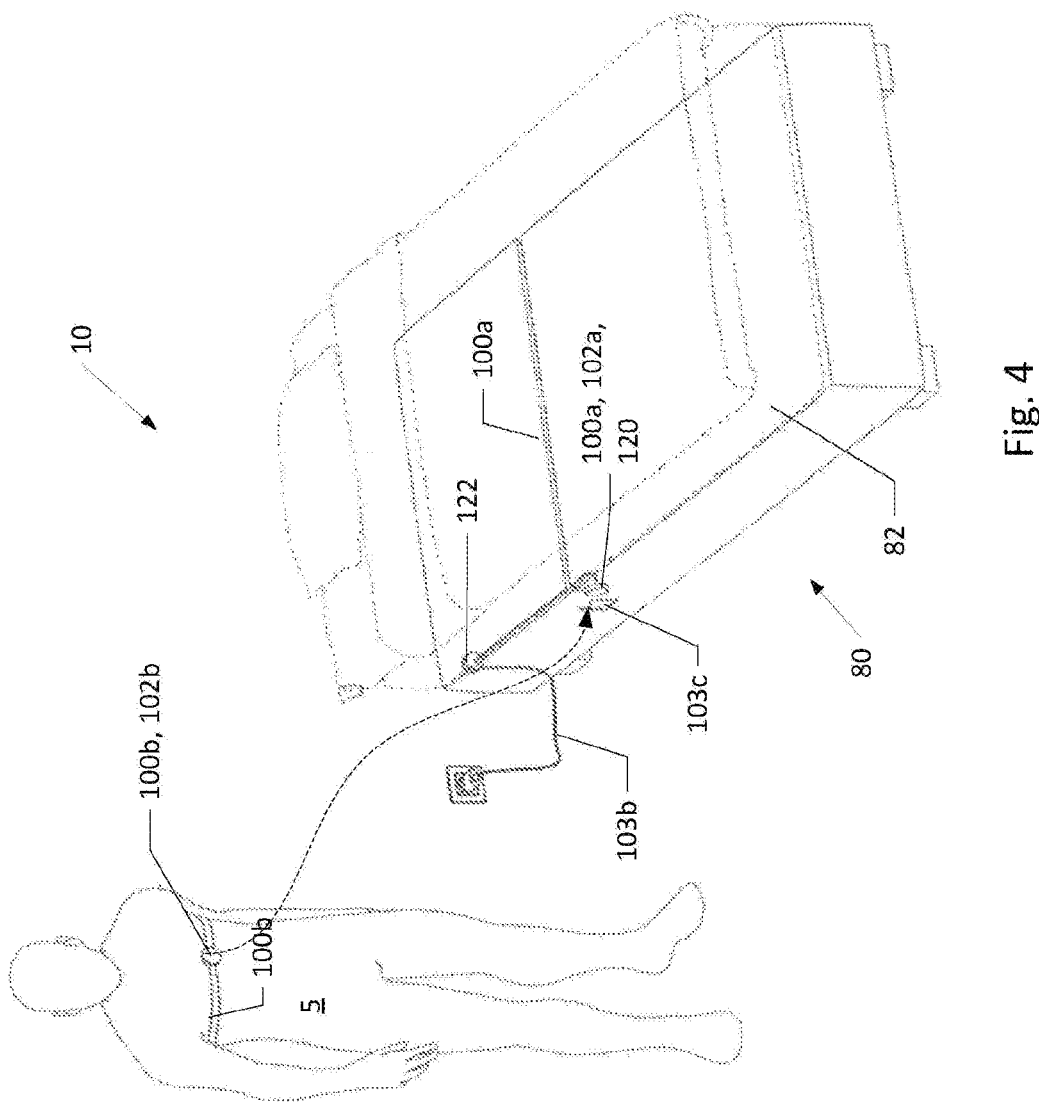
FIG. 4 is a schematic diagram of a health data system that includes one or more sensors disposed to record quantitative health data continuously over time in accordance with one or more embodiments of the present invention.

As shown in FIG. 4, a system manager 120 is embodied in stationary device 102a is disposed on a side of bed 80, next to a pocket 103c. Wearable tracker 102b, in the form as taught herein, is placed during the night in pocket 103c and is preferably contactlessly charged by system manager 120 while system manager 122, similar to system manager 120, removed from system manager 120 interfaces with wearable tracker 122.

Figure 5:
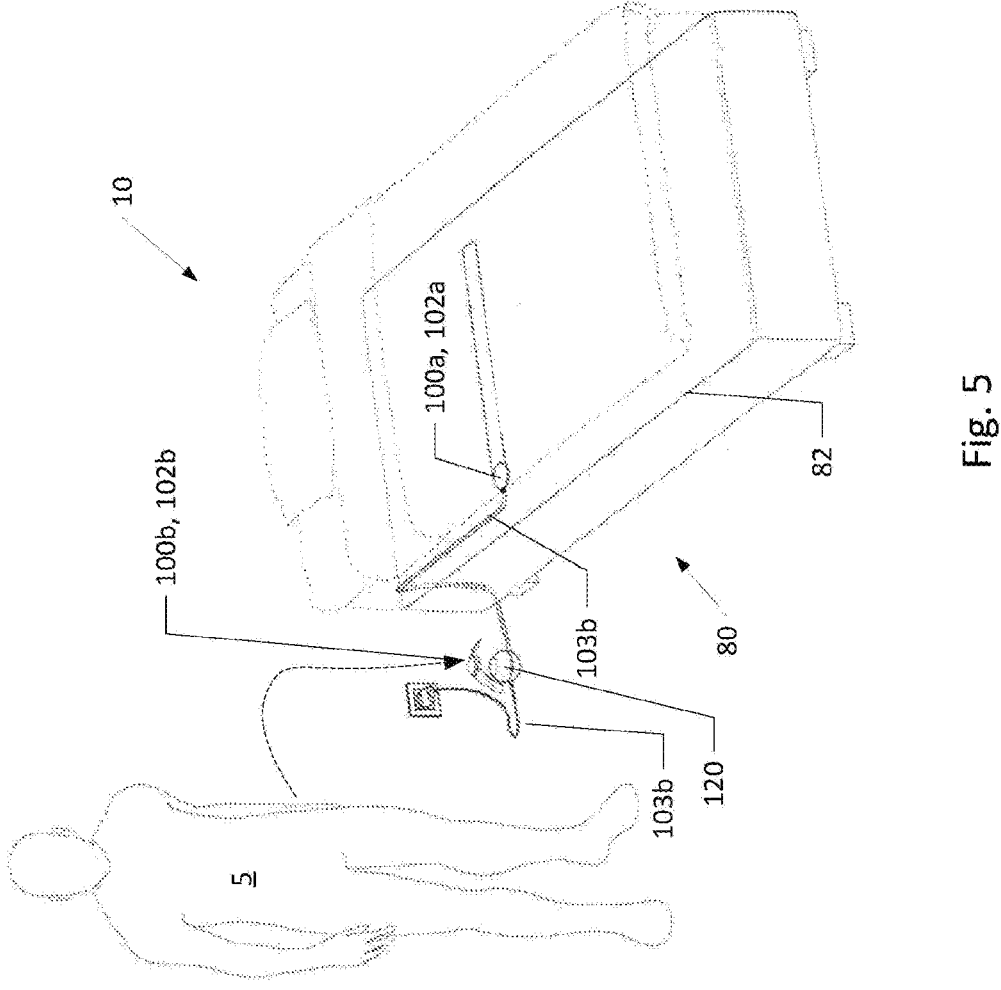
FIG. 5 is a schematic diagram of a health data system that includes one or more sensors disposed to record quantitative health data continuously over time in accordance with one or more embodiments of the present invention.

As shown in FIG. 5, a system manager 120 is embodied in stationary device 102a is disposed on a side of bed 80, and connected via a connection cable 103a to system manager 120. A charging coil 120a. Charging coil 120a is, for example, inductive charging such that wearable tracker 102b is ready for daytime use by the user while away from bed 80. Wearable tracker 102b, in any form as taught herein such as a wristwatch or fitness tracker, is placed during the night in system manager 120 and is preferably contactlessly charged by system manager 120 while system manager 122, similar to system manager 120, removed from system manager 120 interfaces with wearable tracker 122. Therein, system manager 122 may be a smartphone and is connectable to wearable tracker 102*b* through a wireless connection.

Figure 6:
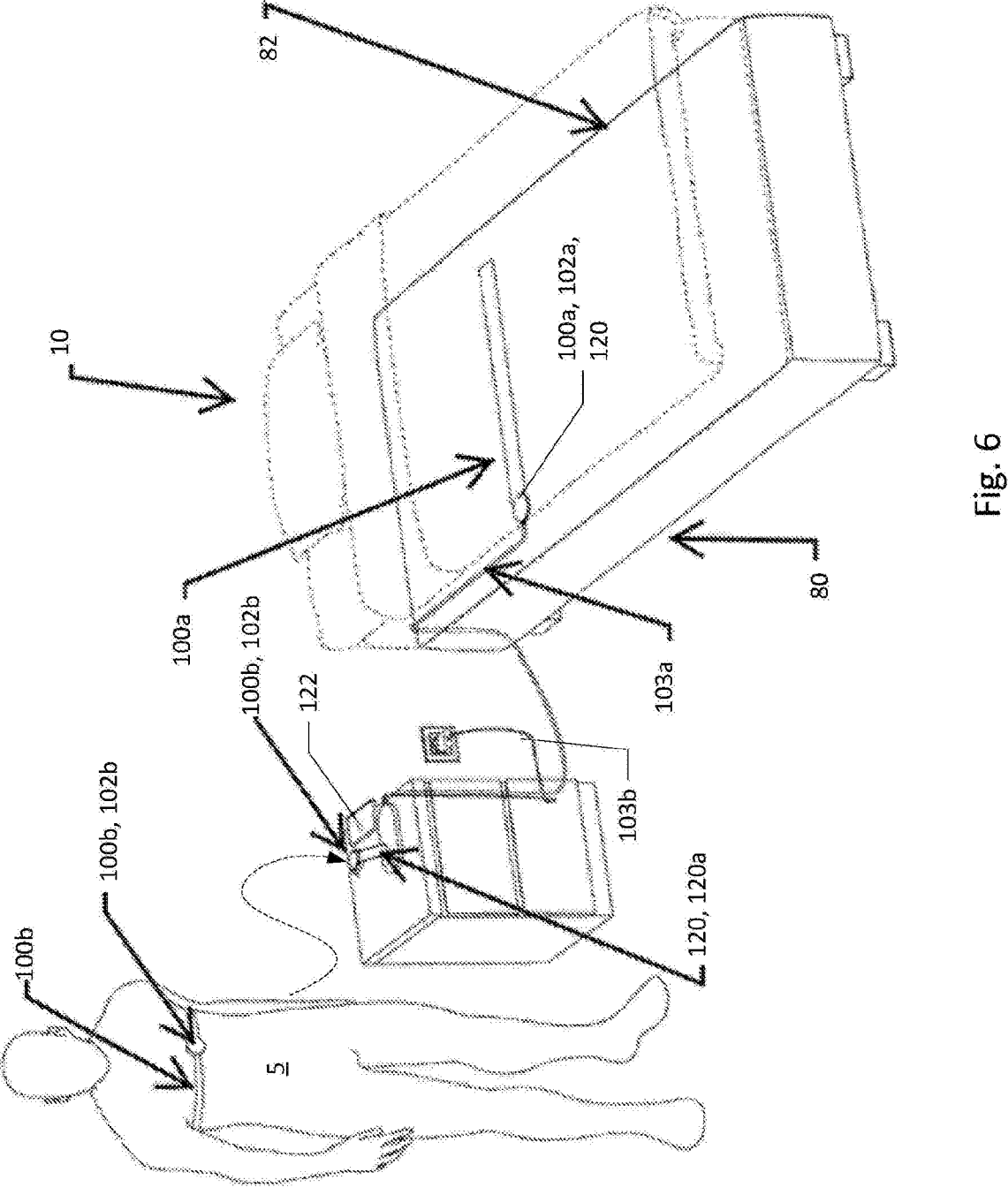
FIG. 6 is a schematic diagram of a health data system that includes one or more sensors disposed to record quantitative health data continuously over time in accordance with one or more embodiments of the present invention.

As shown in FIG. 6, a system manager 120 is embodied in stationary device 102*a* is disposed on a side of bed 80, and connected via a connection cable 103*a* to system manager 120. A charging coil 120*a* is, for example, an inductive charging station such that wearable tracker 102*b* is ready for daytime use by the user while away from bed 80. Wearable tracker 102*b,* in any form as taught herein such as a wristwatch or fitness tracker, is placed during the night in system manager 120 and is preferably contactlessly charged by system manager 120 while system manager 122, similar to system manager 120, removed from system manager 120 interfaces with wearable tracker. Therein, system manager 122 may be a smartphone and is connectable to wearable tracker 102*b* through a wireless connection. Indeed, multiple wearable trackers 102*b* may be used.

Wearable tracker 102*b* houses all signal acquisition as shown in FIG. 6. When the user goes to sleep in the evening, the user places wearable tracker 102*b* on the system manager 120, the bed sensor 100 connected preamplifier electrically (galvanic) or wirelessly connects to wearable tracker 102*b* for signal acquisition. At same time, the wearable tracker 102*b* can stop using its own encapsulated sensor 100*b* which can become electrically disconnected from signal acquisition at same time.

Using same signal acquisition and data sending makes smooth transition at server end for flawless monitoring and/or recording of vital signs. Especially in a double bed used bed sensor easily can be disturbed and wrongly record sleeping from user's spouse who might be sleeping while user is not yet there or has left in the morning earlier. The signal acquisition electronics can sense in many ways, with magnet or via power intake if it is at charging station or on chest. The user simply puts the wearable tracker 102*b* on charging station or removes it when he/she intends to sleep or not. That can create a data event to monitoring software as indicative that user is in bed and has intention to be sleeping or not. It also allows user him/herself lay in bed without intention to sleep, for example, to watch TV or read and, thus, not keeping the wearable tracker 102*b* in charging station indicate that this time should not calculated as the user's sleep time.

For hospital outpatients who usually would use the device up to a week or two and also need to be monitored in very MEMS based inclinometer. Such a position sensor 100*b* could help early detection during the daytime if user 5 has fallen.

Bedding industry is adopting bed sensors as part of mattress or bed platform. In accordance with one or more embodiments of the present invention, the bed sensor electronics 107 with inductive charging available for wearable tracker 102*b* can be installed inside mattress on the side and arrange a pocket 108 outside on it. Then daytime portable sensor 100*b* or wearable tracker 102*b* to be put to the pocket for night to get new charge. Power to the inside mattress electronics, i.e., sensor 100, can be arranged via inductive coil 109 in the mattress end 110

One application is seizure alarming. For example, children with epilepsy may need around-the-clock monitoring. Emfit Oy of Finland has been manufacturing nocturnal seizure monitors since early 2000's. Adding chest monitor as described above would enable effective and easy use around-the-clock monitoring for people with epilepsy. Wearable tracker 102*b* can have small electrodes to sense also sweating which is known to happen upon seizures. If a user wishes to use wearable tracker 102*b* from neck, the laces can have electrodes connected inside to the device electrodes to sense also sweating and not only change in heart rate or fast movement, which happen in tonic-clonic seizure.

The wearable tracker 102*b* with very same ferroelectret sensor can also monitor breathing. Band pass filtered signal 0.1 Hz-3 Hz is especially suitable for that. Its band-pass-filtered signal 6-16 Hz can also be used for diagnosing obstructive and/or central sleep apnea as per earlier listed publications. It is sometimes perhaps enough to use only the wearable tracker 102*b* for such diagnosis as even one night monitoring might be enough.

One embodiment of wearable tracker 102*b* is also to recognize users speech to enable commands, for example, "lights off" or "lights on" at home via an API, for example, connected to iControl platform. There can be small microphone or it is possible to use ferroelectret film sensor as microphone to record users speech and voice recognition chipset transfers that into text. The present invention's wearable tracker can also connect to msart speakers, for example, to Amazon Alexa.

In accordance with one or more embodiments of the present invention, wearable tracker 102*b* comprises ECG electrodes which can be against chest skin or be on the opposite faces of it so that one touches skin of chest and other can be touched with finger. Also necklaces connected to it can be arranged with ECG electrodes. Many MEMS chipsets are available for ECG detecting. When both ECG and BCG signals are obtained, it is possible also to monitor continuously user's blood pressure as per informed in following publications:

www.academia.edu/9141470/
Blood_Pressure_and_Heart_Rate_Variabilities_Estimation_Using_Ballistocardiography or
www.google.fi/url?
sa=t&rct=j&q=&esrc=s&source=web&cd=9&cad=rja&uact=8&ved=0ahUKEwjX0O7LyJrT
AhWIdpoKHSizDU4QFghWMAg&url=http%3A%2F%2Fmelab.snu.ac.kr%2Fmelab%2Flib
%2Fexe%2Ffetch.php%3Fid%3Dresearch%253Apublication%253Aconference%26cache
%3Dcache%26media%3Ddata
%3Abepatch_sas2014_hyun.pdf&usg=AFQjCNF4_FbutDWD1RlS7JvwjCpGnNtzow&sig2=_
PuMXouR7DoMm2ySTzVLWA.

short sequences, perhaps every 30 secs, that heart and breathing rate are okay and user is either in bed (sensed with bed sensor) or is upright and out of bed. The latter can be sensed with wearable tracker 102*b* that has MEMS-based sensor 100*b* that can sense position, using, for example, Different types of sensors and sensor systems may be used. The nighttime sleep sensor 100*a* in the bed can be ballistocardiography principle and sensor 100*b* in daytime wearable tracker 102*b* to provide around-the-clock monitoring can also be even different manufacturer's a smart watch, smart necklace, ring or else. The key to keep a user motivated to tracking or monitoring vital signs is the easy charging of daytime wearable tracker 102b and associated sensor 100b. Therefore the importance is at the nighttime bed sensor system manager 120, for example, placed on the floor or desk 122 or even integrated to the bed platform, is to include charging for daytime wearable tracker 102b and associated sensor 100b, for example, a smart watch from Huawei or Apple. Charging may be performed by an inductive coil and magnet adapted to the top case of the system manager 120, as, for example, in case of Apple watch or it can be also based on having galvanic contacts and magnet adapted on the top case of system manager 120, as, for example, in case of user having Huawei watch.

In accordance with one or more embodiments of the present invention, a user sets the preferred time of the recharge, for example, from 10.00 pm (i.e., 22:00) to 6.00 am (i.e., 06:00).

In accordance with one or more embodiments of the present invention, a sensor 100b in wearable tracker 102b is part of a smart watch to wear on the user's wrist or a ballistiocardiograph device held against the chest of the user. Preferably, it is charged once per day and consequently its battery does not need to be so large since wearable tracker 102b is not used for sleep time health tracking. Thus, the battery is easily charged every night and can be smaller and wearable tracker 102b may be in the form of a smart watch that is can be made thinner. Therein, users prefer smaller and less conspicuous devices.

Sensors

In accordance with one or more embodiments of the present invention, the present invention uses ballistocardiograph technology using a cellular ferroelectret film to convert one or more ballistic movements of the user's heart and one or more breathing movements of the user's lung/lungs into electric output in sensors 100a, 100b. The permanently charged (electroactive) ferroelectret film acts as the operational portion of the sensor or a transducer.

While other sensor technologies may be useful, a ferroelectret film is most suitable due to its simplicity and low cost. A ferroelectret film can be manufactured traditionally using polypropylene (PP) such as that disclosed in U.S. Patent Application Publication 2001/0024712 or U.S. Pat. No. 4,654,546, which are hereby incorporated by reference for all purposes.

A ferroelectret film can be manufactured using COC-POSS-PP or COC-PP as raw material as for example, taught in "Thermally More Durable Electromechanical Films By POSS Nanomodification" by Mika Paajanen, Mikko Karttunen, Satu Kortet, Outi Härkki and Inka Orko of the VIT Technical Research Centre of Finland, Sinitaival 6, FI-33720, Tampere, Finland available at www.vtt.fi/inf/julkaisut/muut/2012/OEEM2012.pdf.

The COC-POSS-PP or COC-PP as raw material is especially suitable because the material remains sensitive in higher temperatures and, thus, enables in-mold encapsulating using only single component polymers in encapsulation. In such way, both small electronics with rechargeable battery can be encapsulated together and resist fluids, including bodily fluids. One of the component plastic compound used in the encapsulation needs to be melted, typically, at 180-200 degrees C., which substantially destroys older PP-based voided ferroelectret film. PP-based ferroelectret films can be encapsulated, however, using a two component materials for potting electronics such as available from Henkel, for example, at www.henkeladhesivesna.com/blog/led-compatible-transparent-potting-materials.

In accordance with one or more embodiments of the present invention, Emfit Oy manufactures ribbon sensor (model code R-19) is used to create the wearable sensor assembly's ballistocardiography sensor 100a, 100b.

As it is easier for user to put a chest belt on the chest so that the plastic connection comes in the middle of chest, and as the whole sensor needed electronics and rechargeable battery takes some area in length and width, the electronics are placed so that they come on side of the chest, for example, right side, and the actual R-19 ribbon type sensor is connected to it. The last in the assembly is the Li-Po battery, connected with durable wires to the electronics, and housed so that twisting the assembly would not break them a part. The battery and wires, along with electronics, should be protected against punching with for example, aramid webbing. The R-19 sensor is long and continues behind users back on the chest, on the heart, i.e. left side. The actual area to pick up heart's beats by ballistic principle is achieved so that several folds are done, for example, so that six (6) layers are in total against heart area on chest.

In accordance with one or more embodiments of the present invention, the ribbon sensor is shorter and does not reach behind the users back. To avoid disturbance to the signal, the length before the folded area is heated in production to for example, 160 C degrees so that the eletromechanical response is nulled. What however is achieved is one simple construction that is easy and low cost to produce. The whole assembly is inserted inside a tubular webbing made from fire resistance threading and can be waterproof and both ends are sealed. The inductive charging allows this (no need for example, USB connector to charge the battery). The other sensors for the whole product (temperature, accelerometer etc.) are arranged into same printed circuit board as the signal acquisition for the BCG sensor (R-19). Into the end of assemble, either battery end or folded end, a loop is arranged. The assembly with tubular webbing is further placed inside an elastic, reusable but for single user intended sock, that is elastic in its length especially, and is waterproof. As the BCG sensor is not easy to arrange because it is not elastic in its length, the sock provides elasticity needed for user movements. It can be low cost and be replaced between users to avoid contamination. The BCG sensor being thin and flexible and but slippery as it would be for example, built on polyester, can move inside the sock preferably being tightened to one end of the elastic sock.

In one embodiment of this new innovation, the BCG bed sensor (can be used for wearable chest sensor as well) is manufactured so that it has preferably two polyester or other plastic films that carry the electrodes and the electromechanical ferroelectret made from BOPP (for example, can be BOPP-COC as well, or PVDF or other electromechanically active material) is arranged in between them. In the referred manufacturing method where aluminum foil or copper foil with polyester is etched to provide patterning for Emfit® sensor, the third (polyester/aluminum or polyester/copper) layer can be avoided if the whole length provides a loop (204, similar as in FIG. 11d) where both ends come to the electronics printed circuit board 208. The signal electrode (similar as in FIG. 11d, 403) is arranged narrower in its width, from both sides. The ground electrode (similar as in FIG. 11d, 404-405) on the other side is whole width. In the manufacturing process is achieved for example, 600 mm reel-to-reel laminated material where on both outsides there is 23 microns copper, next towards middle there are 25 microns polyester and in the middle there is the electro active materials such as ferroelectret BOPP, or PVDF. Onto that laminated material has been etched figures of 30 signal electrode strips on one side of the laminate, and the other side, becoming ground electrodes, is no etched figures. The whole laminated reel, in process for example, 250 meters long, is then cut into 30 narrow strips of 19 mm wide, where one side has signal electrode being for example, about 10 mm in width and positioned in the middle section, and other side has ground electrode being whole width. In the etching, following lamination and longitude cutting is then achieved 30 pcs 19 mm wide ribbons, being 250 meters long. Each ribbon can be then cut to for example, about 2.8 meter long. The advantage of this new process is that the lamination of electroactive material with electrodes (carried on polyester or can be polyimide or other plastic) is arranged first and later is the actual etching. Then the achieved ribbon 204, with signal on one side and ground on other side and electro-active material in center, is first folded into two 201, 203, where the signal electrode comes to center (two signal electrodes face each other) and outer layers are ground layers. Then the folded end 202 is further folded 3 times from 10 cm length 203. Then that end has total 6 layers and signal electrode does not show outside and is thus shielded from electromagnetic interference. Then the whole assembly comes about 1 meter in total length, and has two layers continuing to the other (electronics) end 208. Preferably, preferably one end of these is connected to the electronics; however, both can be. The layers reaching the electronics 208 are not preferably glued together. That they are not glued and only one end of the two layers is connected to electronics provides better flexibility without layers becoming separated from each other as the radius changes, when user place it over his/her body or folds into carry-on bag. The area with 6 layers is then the one that comes against users heart area. Inside the tubular webbing, each layer stays close, i.e. is adjacent or preferably touching, to each other and can be further inserted inside a shrink tube to create perfect moisture protection to avoid electrodes corrosion. Since the number of active layers is many, the sensitivity increases significantly.

In accordance with one or more embodiments of the present invention, the ribbon sensors are produced so that first one or can be two or more ferroelectret films are laminated to each other. If two, there can be preferably one for example, 25 microns PET layer laminated in between. To the outer sides is then laminated metal foil, copper or aluminum (copper is preferred due better strength) about 9 to 23 microns thick. The metal is first preferably arranged on a very thin, for example, 25 microns polyester or polyimide, which later is far more expensive and its better properties are rarely needed. The metal electrodes are arranged in the final laminate so that are exposed on outer layers. The whole laminate is produced reel to reel for example, 600 mm in width. The achieved laminate is then first cut into for example, same 19 mm width ribbons. To achieve arrangement where signal electrode cannot get shorted to ground layer from around edges, one layer is arranged to go through mechanical abrasion where metal material is removed from edges. It is enough to remove for example, 3 mm from both edges, on one side of the ribbon. It is possible also to remove preferably two narrow, for example, 1 mm in width, kind like grooves. Then the 1 mm provides enough creeping distance and separation between ground and signal electrode. On the edges remaining narrow metal areas are in the electronics connected through the substrates and become connected to the ground layer on the other side of the whole ribbon. In whole, this method of manufacturing provides environmentally improved method as no acids are needed and toxic waste is not produced. The abrasion of metal is pure metal dust and be collected for reuse.

Referring to FIGS. 12*a* and 12*b*, in accordance with one or more embodiments of the present invention, a whole new ribbon type BCG sensors for use in bed or on a wearable device as example against chest to sense both heartbeat (ballistocardiogram) and breathing, or onto arm to sense movement and pulse pressure on peripheral artery, is achieved with lowest possible cost per meter and most environmentally economic way to avoid material waste, use of acids (etching), and dust (abrasion) during manufacturing, as follows. Similar to earlier explained, first one or can be two or more ferroelectret films (801) are laminated to each other. If two, there can be preferably one for example, 25 microns PET layer laminated in between. To the one outer side only is then laminated metal foil (802) which is preferably first laminated on polyester (803) (or polyimide or else). Metal is as example copper or aluminum (copper is preferred due better strength) about 9 to 23 microns thick. The carrying layer (803), polyester (or else) comes in between electroactive ferroelectret (802) or PVDF or else and metal foil (802) comes then on one outside. The whole laminate is the cut lengthwise into ribbons as example 19 mm in width. It is not etched, preferably but preferably cut into narrow ribbons. Secondly similar metal foil (802) (23 microns copper as example) on a carrying substrate (803) (25 microns polyester as example) is cut into 13 mm width ribbons. Sensor can be arranged so that the 13 mm ribbon, metal face, with is arranged to come against the electroactive material on one side of the 19 mm wide ribbon. To stay in the middle it is attached (804) by adhesive or other simple means from here and there against the 19 mm ribbons electroactive material face. This whole length is then folded into half-length, into kind of loop, similar as earlier explained. Then outer layers that are 19 mm wide metal provide shielding for 13 mm wide signal electrode in the center. It is also possible first to cut the laminate with electroactive material into for example 38 mm wide ribbons 805. In a lengthwise folding machine then fold it lengthwise so that electroactive material is inside, the two faces against each other. Then take for example 16 mm wide ribbon 806 of metal on a thin carry-on substrate such as polyester. Insert this 16 mm wide metal/polyester ribbon inside the now 19 mm width folded ribbon as deep as it goes. The 16 mm ribbon will be the signal electrode, and comes inside the two ground layers achieved with folding the 38 mm wide ribbon. In this embodiment, two electroactive material layers are exposed in between two ground layers and have signal layer in the center of them. The one edge 807 where there is 3 mm of the electroactive film on the carry-on polyester substrate, it can for example be welded together with ultrasound or simply the whole sensor is inserted inside a shrink tube that shrinks in low temperature for example 80 C. This embodiment is most economic for environment but also to very low cost to manufacture.

The whole assembly, i.e., health data system 10 and other features can be used also for animals, For example, canine, to measure their vitals signs For example, after surgery or in home, For example, if canine has epilepsy and need to be left alone for daytime. It is easy to arrange a vest that canine can carry, as is shown in FIG. 11*b*.

The innovation comes in length such that it can be placed for during nighttime under mattress and become non-contact, non-wearable nighttime monitor. It can protrude from under mattress so that inductive charging can be provided to it while sleeping and it can measure in same time. In the morning when the user wakes up, the user can remove the monitor from under the mattress and attach it on the chest, that is the stationary sleep monitor and the wearable tracker are a single unit for inherent convenience. Therein, the battery is designed, for example, to last to up to about 18 hours which is sufficient for putting it back under the mattress when user goes again to sleep and let it charge.

In one or more embodiments of the present invention, there are two Li-Po batteries, each being capable to provide a large enough charge for one full day's use. Charging is arranged so that always one battery only is charged over the night, so that every second day one battery is used and charged. By having two batteries, the expected use time in days is doubled. One battery can be charged about 600-700 times. Then the expected life is increased to about 1200-1400 days.

In one or more embodiments of the present invention, there are two ferroelectret electromechanical ribbons. Another one is much longer, and folded several times, to provide for example, in total 4 or even 6 meters of length. As the user body moves and breathing expands chest, the movement also produces charge as is known. It can be arranged that this another ribbon produces charge from movement and it is used to the Li-Po battery. Then Li-Po can be smaller to achieve necessary use time. If actual measurement is done enough rarely, it is in theory possible to achieve assembly that does not need external charging.

Stationary Sensor Device

Figure 8A:
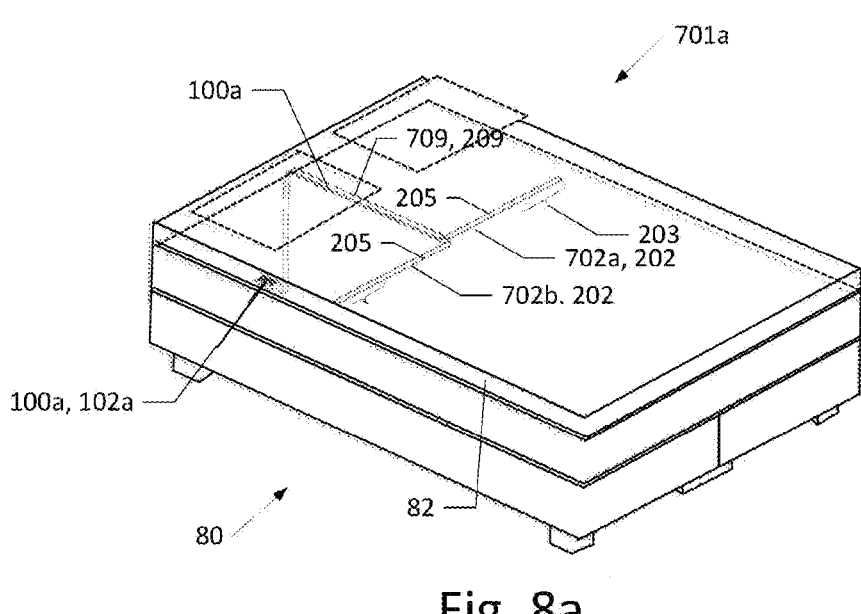
FIGS. 8a-8d are schematic diagrams of a layout of the stationary sensor in accordance with one or more embodiments of the present invention.
Figure 8B:
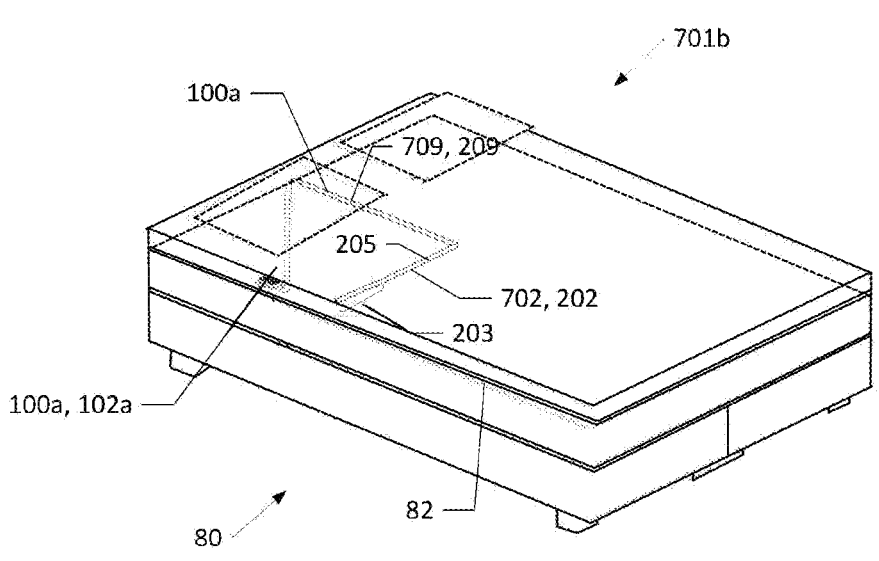

FIG. 8a is a schematic diagram of a stationary sensor device and a sensor in accordance with one or more embodiments of the present invention. FIG. 8b is a schematic diagram of a stationary sensor device and a sensor in accordance with one or more embodiments of the present invention.

In accordance with one or more embodiments of the present invention, it is preferred to reduce the number of associated components to lower the costs. One such is the cable between stationary sensor device 102a having a sensor 100a and system manager 120.

Figures 7A, 7B:
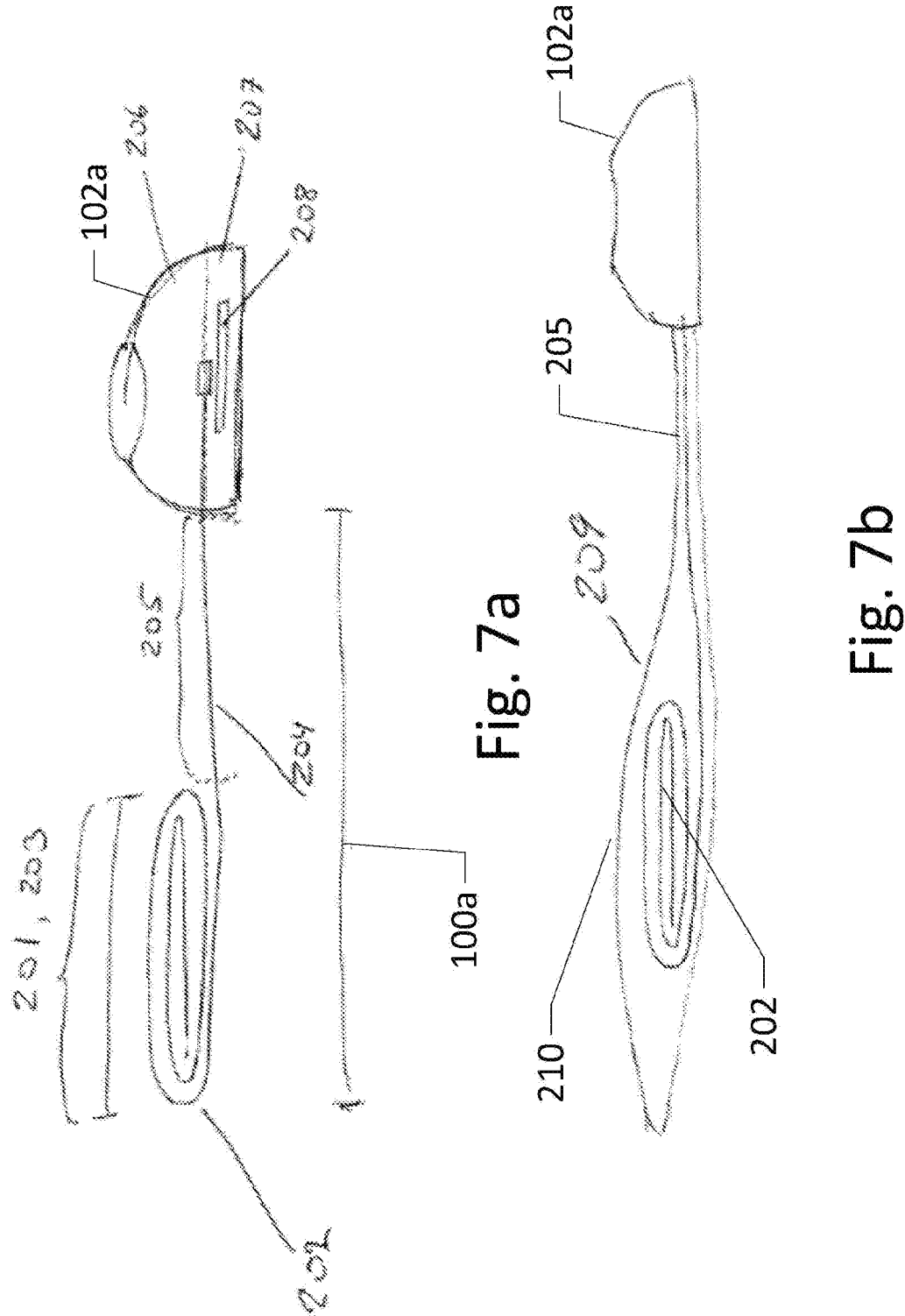
FIGS. 7a and 7b are schematic diagrams of a construction of a stationary sensor in accordance with one or more embodiments of the present invention.

As shown in FIG. 7a, in the lower cost embodiment, the sensor 100a is arranged as previously explained new kind ribbon type ferroelectret or pvdf sensor without using etching, or using etching as is state-of-art manufacturing method by Emfit Oy. Therein, a width of 19 mm is well suited for the present application. The ribbon sensor 100a is folded many times over itself to form, for example, a 30 cm length 201, and thus arranging two or more, preferably 5 or 6 layers in a plural layer sensor ribbon 202. Then it sufficiently provides enough active sensor area 203 but is short enough to fit well under a sleeping person. Instead of using cable 103a causing cost and labor, ribbon sensor 100a can continue to the floor with extension area 204, which is for example about 120 cm in length of segment 205, and go between the system manager plastic halves 206, 207 of the housing and connect directly into printed circuit board assembly 208 of sensor 100a.

As shown in FIG. 7b, advantageously, the expense and labor of making cable connections into two ends can be avoided. The sensor is insertable inside a tubular webbing 209 to improve feel and look and provide improved mechanic durability and can be inserted inside shrink tubing to create good waterproofing. The sensor can also be made of round or oval type C-series sensor cable from Emfit Oy of Finland. It is important to place sensor section 202 under the user in order to produce strong signal, especially while other portions of sensor 100a are hanging free in air and not under mattress. For example, in accordance with one or more embodiments of the present invention, an inactive sensor section 205 is not going to be under person in bed, and thus to inactivate is heated to over 100 C degrees, preferably to about 160 C degrees which is when the as example BOPP based electro active material melts and it looses its capability to produce electric signal from vibrations. Then the manufacturing process is simple and cost effective.

As shown in FIG. 8a, a sensor 100a comprises two-sensor arrangement 701a for two user monitoring. A first sensor monitoring side 702a that includes a first active sensor area 203 that is opposite a second active sensor area 203 on second monitoring side 702b so as to have two specific sensing areas that are separated. Each monitoring side 702a, 702b comprises an inactive sensor section 205 is disposed close to middle to avoid picking up stray signals from the other user and is configured plural layer arrangement ribbon 202. A central monitoring section 709 carries each monitoring side 702a, 702b to stationary device 102a. Central monitoring section 709 comprises the tubular webbing 209.

As shown in FIG. 8b, a sensor 100a comprises single sensor arrangement 701b for a single user monitoring. A monitoring side 702 includes a first active sensor area 203. Monitoring side 702 comprises an inactive sensor section 205 is disposed close to middle to avoid picking up stray signals and is configured plural layer sensor ribbon 202. A central monitoring section 709 carries monitoring side 702 to stationary device 102a. Central monitoring section 709 comprises a tubular webbing 209.

Figure 8C:
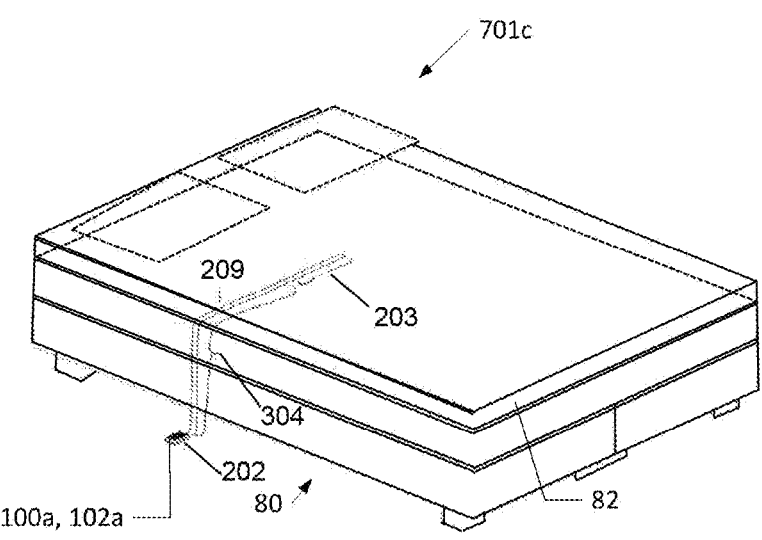

As shown in FIG. 8c, a sensor 100a comprises single sensor arrangement 701c for a single user monitoring. In accordance with one or more embodiments of the present invention, two tubular webbings end into the same electronics with signal acquisition for them both. However, it is also possible to arrange so that one tubular webbing has inside two ribbon sensors 204,203, simply one longer extension area 204 to reach to further side of the mattress.

Figure 8D:
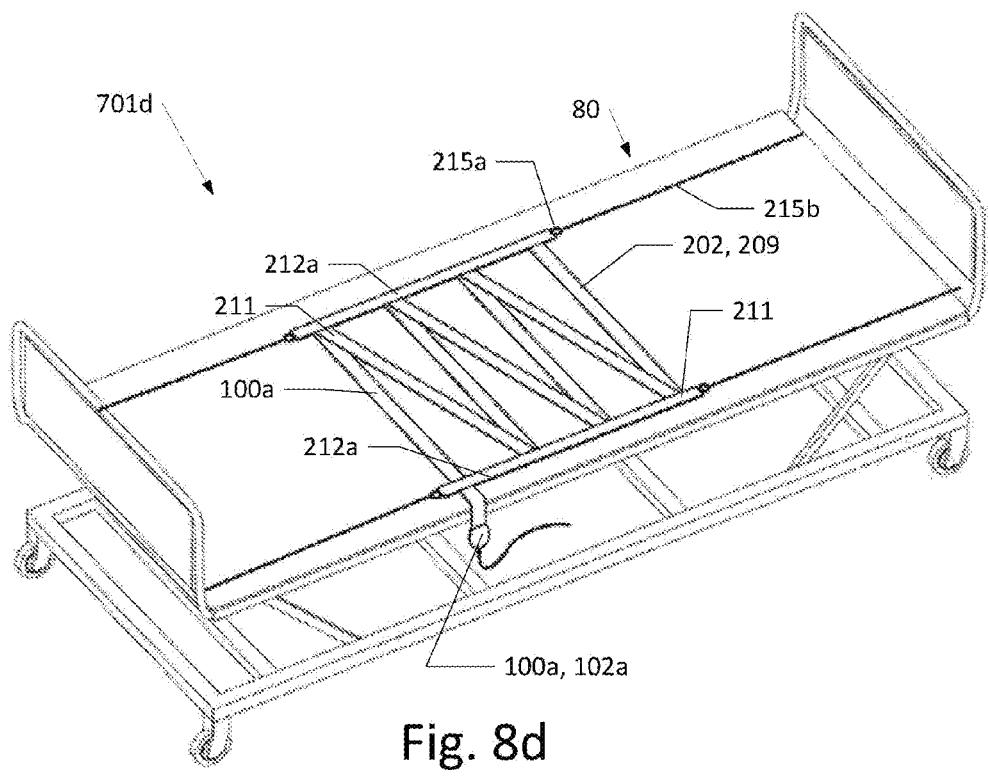

As shown in FIG. 8d, a sensor 100a comprises single sensor arrangement 701d for a single user monitoring. A sensor 100a is disposed on a bed 80, such as a hospital bed and comprises one or more z shapes, i.e. zig-zag between two sides of the bed, using a sensor ribbon, preferably a plural layer sensor ribbon 202, inside tubular webbing 209 for longevity. FIGS. 9a and 9b illustrate the making of the corners 211. A tubular webbing 209 is connected using uneven lengths 209a, 209b to a substrate 212 comprising a first portion 212a and a second portion 212b. The sensor ribbon is then folded at angle to form corner 211. Substrate portion 212a is then folded over portion 212b sandwiching the folded ribbon sensor. The assembly is secured via connections 209c. In FIG. 8d, a substrate 212 is tensioned to the bed frame using tension lines 215b and connectors 215a. Thus, advantageously, sensor 100a is positioned to obtain sensor readings from the bed regardless of the user's position.

Wearable Tracker

In accordance with one or more embodiments of the present invention, to permit 24/7 (around-the-clock) health tracking, the wearable tracker 102b comprises a plurality of rechargeable batteries 501, 502 (shown for example in FIG. 10c). Each battery recharges according to a predetermined time schedule, preferably, each occurrence of recharging occurring at a time of low-usage such as nighttime.

For example, a wearable tracker 102b includes two rechargeable batteries 501, 502. By having two batteries, the expected use time in days is doubled. Each being capable to provide a large enough charge for one full day's use. Charging is arranged so that always one battery only is charged over the night, so that every second day one battery is used and charged. That is, each of the two rechargeable batteries is charged every second night. Thus, for example, when a Li-Po battery usually is good for about 600-700 charges, with two batteries the device useful life can be extended to have twice the life, up to 1200-1400 days in total use.

Wearable tracker 102b houses all signal acquisition as shown in FIG. 10a, 10b. When the user goes to sleep in the evening, the user places wearable tracker 102b on the system manager 120, the bed sensor 100 connected preamplifier 503 using an electrically (galvanic) contact 504 or wirelessly connects to wearable tracker 102b for signal acquisition. At same time, the wearable tracker 102b can stop using its own encapsulated sensor 100b, which can electrically become disconnected from signal acquisition at same time.

Using same signal acquisition and data sending makes smooth transition at server end for flawless monitoring and/or recording of vital signs. Especially in a double bed used bed sensor easily can be disturbed and wrongly record sleeping from user's spouse who might be sleeping while user is not yet there or has left in the morning earlier. The signal acquisition electronics can sense in many ways, with magnet or via power intake if it is at charging station or on chest. The user simply puts the wearable tracker 102b on charging station or removes it when he/she intends to sleep or not. That can create a data event to monitoring software as indicative that user is in bed and has intention to be sleeping or not. It also allows user him/herself lay in bed without intention to sleep, for example, to watch TV or read and thus not keeping the wearable tracker 102b in charging station indicate that this time should not calculated as the user's sleep time.

For hospital outpatients who usually would use the device up to a week or two and also need to be monitored in very short sequences, perhaps every 30 secs, that heart and breathing rate are okay and user is either in bed (sensed with bed sensor) or is upright and out of bed. The latter is sensed with wearable tracker 102b that has MEMS-based sensor 100b that can sense position, using, for example, MEMS based inclinometer. Such a position sensor 100b could help early detection during the daytime if user 5 has fallen. Other MEMS sensors that can be incorporates inside the wearable device are ECG, temperature, and SpO2.

Wearable tracker 102b need a signal link using Wi-Fi or cellular data network. These transmissions needs consume so much power that needed size battery is not feasible inside the actual against chest wearable device. It is normal to use smartphone sending data from a wearable device with low power Bluetooth to a smartphone that user carry with, and via it further to server where data is available for analysis system that can generate alarms for caregivers. Since it is recommended that outpatients walk and live normally as it improves healing, performing daily activities such as going food shopping can easily be necessity and healing for practical reasons as well. However, a user's own phone is not necessarily the best means to achieve consistent monitoring, for example, frequent 30-second interval data transmissions to a monitoring station or using AI software to generate alarms for possible deterioration or fall. Thus, a more robust device is preferred and preferably developed to be as independent as possible. This also advantageously would meet software development requirements for medical devices since it is safer than using smartphones for it. At home, a Wi-Fi setup of a standard consumer device might also be a challenge and be problematic from usability and technology adaption points of view.

Thus, in accordance with one or more embodiments of the present invention, as shown in FIG. 10c it is useful that the signal acquisition (for bed sensor 100a and chest sensor 100b) only have a small power transmitter such as Bluetooth Low Energy (BLE) 520. There should then be additional device 104 with 3G/LTE 522 connectivity to receive the vital signs data with low energy consumption technology BLE as the wearable tracker 102b cannot have large enough battery to keep it comfortable. A wearable system manager acts as signal repeater 104 having a 3G/LTE and WI-Fi connectivity. It can be large enough, as it would preferably be taken, for example, to pocket while going out. It can then house enough large battery for good full day or even several days operation. It can be charged at charging station 122 at nighttime. In this kind embodiment user simply, when going to sleep, install the small size 3G/LTE enabled device 104, also with inductive charging, to charging station 122.

The stationary sensor 102a can have a small signal acquisition and BLE transceiver inside the connector 106 between power cable and sensor. User charge also the portable sensor 102b or wearable tracker 102b at the same system manager 122. Then bed sensor has its own BLE enabled signal acquisition 106 and its data flow is continuous and never stopped. It is also possible to have device 104 have two charging coils. One on its bottom to come against inductive charging station 122, and one on the top (other side) to provide charging for the wearable tracker 102b so they can be at night on top of each other.

In accordance with one or more embodiments of the present invention, a sensor 100b in wearable tracker 102b is part of a smart watch to wear on the user's wrist or a ballistocardiography device to be held against the chest of the user. Preferably, it is charged once per day and consequently its battery does not need to be so large since wearable tracker 102b is not used for sleep time health tracking. Thus, the battery is easily charged every night and can be smaller and wearable tracker 102b may be in the form of a smart watch that is can be made thinner. Therein, users prefer smaller and less conspicuous devices.

In accordance with one or more embodiments of the present invention, to permit 24/7 (around-the-clock) health tracking, the wearable tracker 102b comprises a plurality of rechargeable batteries, each recharging according to a predetermined time schedule, preferably, each occurrence of recharging occurring at a time of low-usage such as nighttime. For example, a wearable tracker 102b includes two rechargeable batteries. Each of the two rechargeable batteries is charged every second night. Thus, for example, when a Li-Po battery usually is good for about 600-700 charges, with two batteries the device useful life can be extended to have twice the life, up to 1200-1400 days in total use.

In one or more embodiments of the present invention, there are two Li-Po batteries 501, 502. Each being capable to provide a large enough charge for one full day's use. Charging is arranged so that always one battery only is charged over the night, so that every second day one battery is used and charged. By having two batteries, the expected use time in days is doubled. One battery can be charged about 600-700 times. Then the expected life is increased to about 1200-1400 days.

Referring to FIGS. 11a-11d, In one or more embodiments of the present invention, Emfit Oy manufactured ribbon sensor (model code R-19) is used to create the wearable sensor assembly's ballistocardiography sensor. As it is easier for user to put a chest belt 300 on the chest so that the plastic connection 301 comes in the middle of chest, and as the whole sensor needed electronics and rechargeable battery takes some area in length and width, the electronics 302 are placed so that they come on side of the chest, as for example right side, and the actual R-19 type sensor 100*b* is connected to it. The last in the assembly is the Li-Po battery 303, connected with durable wires 304 to the electronics 302, and housed so that twisting the assembly would not break them a part. The battery and wires, along with electronics, should be protected against punching with as, for example, aramid webbing.

The ribbon sensor is long and continues behind users back on the chest, on the heart i.e. left side. The actual area 203 to pick up heart's beats by ballistic principle is achieved so that several folds 202 are done, for example, so that 6 layers are in total against heart area on chest. To avoid disturbance to the signal, the length 204 before folded area is heated in production to as for example 160 C degrees so that the electromechanical response is nulled. What however is achieved is one simple construction that is easy and low cost to produce. The whole assembly is inserted inside the tubular webbing 209 can be made waterproof with polyure-thane and is made from fire resistance threading and both ends are sealed. The inductive charging allows this (no need for example USB connector to charge the battery). The other sensors for the whole product (temperature, accelerometer etc.) are arranged into same printed circuit board 302 as the signal acquisition for the BCG sensor (R-19).

Into the end of assemble, either battery end or folded end, a loop is arranged. The assembly with tubular webbing is further placed inside an elastic, reusable but for single user intended sock, that is elastic in its length especially, and is waterproof. As the BCG sensor is not easy to arrange be elastic in its length, the sock provides elasticity needed for user movements. It can be low cost and be replaced between users to avoid contamination. The BCG sensor being thin and flexible and but slippery as it would be as for example built on polyester, can move inside the sock preferably being tightened to one end of the elastic sock.

System Manager

Referring to FIGS. 1-6, system manager 120 receives quantitative health data from sensor 100*a* and monitors the user's vital signs at nighttime using quantitative health data and/or an evaluation of qualitative health data. System manager 120 sends quantitative health data from sensor 100*a* to an internet cloud and from there with an application programming interface (API) to a central monitoring server or device that helps evaluate or determine the qualitative health data, generally referred to as a "monitor".

In accordance with one or more embodiments of the present invention, system 10 comprises a computing device (not shown) that operates one or more artificial intelligence programs for analysis and smart notification of, for example, heart rate and or breathing rate changes that potentially indicate one or more deteriorating conditions of the user.

The one or more artificial intelligence (AI) programs may also record and store quantitative health data from for heart arrhythmia detection and perform diagnosis to replace the golden standard Holter measuring which is based on skin contact ECG sensing. One important need is also diagnosing of sleep apnea as discussed in publications available at ampub.uta.fi/bitstream/handle/10024/99487/screening-_sleep_disordered.pdf or tutcris.tut.fi/portal/files/2985241/tenhunen_1304.pdf.

Referring to FIGS. 10*a*-10*b*, while being used during the daytime, wearable tracker 102*b* calculates the user's heart rate, breathing rate, heart rate variability and movement activity from quantitative health data obtained by sensor 100*b* and sends the quantitative health data via included BLE (Bluetooth Low Energy) or WI-Fi module. Other methods can also be used, such, or example, the method used by Zigbee. Preferably, these are based on BCG prin-ciple. Therein, a chest BCG sensor 100*b* can be also com-prise a MEMS-based accelerometer, for example, from Murata and temperature sensor.

Even and under bed installed sensor 100*a* can be similarly based on MEMS. One of the innovative steps of system 10 is to allow nighttime charging for wearable tracker 102*b* by the nighttime portion of health data system 10 when the user goes to bed.

In accordance with one or more embodiments of the present invention, a same signal acquisition and wireless transceiver for both nighttime and daytime data sending may be used. The small on chest placed device can house the sensor signal acquisition and data transmission also for nighttime use. The bed sensor cable end of system manager 120 can only have preferably first stage preamplifier and inductive charging electronics and connect to wall electric outlet for receiving power.

Preferably, system managers 120 and 122 are each equipped with a charging coil, for example, inductive charg-ing such that portable sensor 100*b* is ready for daytime use by the user while mobile and away from bed 80. Portable sensor 100*b* may be any suitable portable sensor but pref-erably is a chest sensor worn on the user's chest and/or utilizes small ballistocardiography as used in sensor device 100.

When the user leaves the bed in the morning, the user takes portable sensor 100*b* and can hang sensor 100*b* on his/her neck or slip on a chest strap or into a small pocket on a shirt placed against area of heart. During night, system manager 120 is charging sensor 100*b* for daytime use.

System manager 120 senses and monitors user's vital signs at nighttime and sends it to cloud and from there with API to monitoring central. In accordance with one or more embodiments of the present invention, artificial intelligence may be used for smart notifying of, for example, heart rate, and or breathing rate change that potentially could lead to deterioration. It could be also needed for preferably to record and store ballistocardiogram for heart arrhythmia detection and diagnosis to replace today's golden standard Holter measuring which is based on skin contact ECG sensing. One important need is also diagnosing of sleep apnea as dis-cussed at publications ampub.uta.fi/bitstream/handle/10024/99487/screening_sleep_disordered.pdf or tutcris.tut.fi/por-tal/files/2985241/tenhunen_1304.pdf.

While being used during the daytime, portable sensor 100*b* measures and calculates user's heart rate, breathing rate, heart rate variability and movement activity and sends the data via included BLE or WI-Fi module. Other methods can also be used such for example, the method used by Zigbee. All this can be based on BCG principle. The chest BCG sensor can also be MEMS based accelerometer For example, from Murata. Even under bed installed sensor can be similarly based on MEMS. One of the innovative steps of this new whole system is to allow nighttime charging for daytime device, at nighttime sensor system, when users go to bed.

While the invention has been described in conjunction with specific embodiments, it is to be understood that many alternatives, modifications, and variations will be apparent to those skilled in the art in light of the foregoing description.

What is claimed is:

1. A system for monitoring quantitative health data of a user, the system comprising:
   a stationary sensor device for monitoring a first set of quantitative health data of the user when the user is resting in bed; and
   a wearable tracker for monitoring a second set of quantitative health data of the user when the user is away from bed, the wearable tracker comprising a rechargeable power source;
   wherein the wearable tracker is configured to be worn by the user and becomes disconnected from signal acquisition of the second set of quantitative health data of the user when the rechargeable power source is being charged;
   wherein the first set and the second set are sequential in time to obtain around-the-clock monitoring of the quantitative health data of the user,
   wherein the first set and the second set do not overlap in time;
   wherein the stationary sensor device comprises a sensor, the sensor comprises a ferroelectret film having an active sensor section, the active sensor section is configured to be placed proximate to the user;
   wherein the active sensor section comprises a plurality of ferroelectret film layers for increased sensitivity.

2. The system of claim 1, further comprising a system manager comprising a computing device for acquiring the first set of the quantitative health data of the user from the stationary sensor device.

3. The system of claim 2, wherein the computing device acquires the second set of the quantitative health data of the user from the wearable tracker.

4. The system of claim 1, wherein the charger is an inductive charger.

5. The system of claim 1, wherein the sensor of the stationary sensor device is the first sensor and the wearable tracker comprises a second sensor, the first sensor and the second sensor comprising different sensor types.

6. The system of claim 5, wherein the second sensor comprises microelectromechanical system.

7. The system of claim 1,
   further comprising
      a first system manager comprising a first computing device for acquiring the quantitative health data of the user from the stationary sensor;
      a second system manager comprising a second computing device for acquiring quantitative health data of the user from the stationary sensor.

8. The system of claim 1, wherein the stationary sensor device further comprises an inactive sensor section of the ferroelectret film, the inactive sensor section being proximate to an interference source.

9. The system of claim 1,
   further comprising a webbed tubing,
   wherein the active sensor section is disposed in the webbed tubing to protect from damage.

10. The system of claim 1, wherein the wearable tracker is selected from a smartphone, a watch, or a chest-worn device.

11. The system of claim 1, wherein the plurality of ferroelectret film layers for increased sensitivity is at least two layers.

12. The system of claim 11, wherein the plurality of ferroelectret film layers are formed by folding the ferroelectret film over itself.

13. The system of claim 1, wherein the plurality of ferroelectret film layers are formed by folding the ferroelectret film over itself.

14. The system of claim 1, wherein the plurality of ferroelectret film layers are formed by folding the ferroelectret film over itself in a C shape.

15. The system of claim 1, wherein the plurality of ferroelectret film layers are formed by folding the ferroelectret film over itself in a spiral shape.

16. A system for monitoring quantitative health data of a user, the system comprising:
   a stationary sensor device for monitoring a first set of quantitative health data of the user when the user is resting in bed; and
   a wearable tracker for monitoring a second set of quantitative health data of the user when the user is away from bed, the wearable tracker comprising a rechargeable power source;
   wherein the wearable tracker is configured to be worn by the user and becomes disconnected from signal acquisition of the second set of quantitative health data of the user when the rechargeable power source is being charged;
   wherein the first set and the second set are sequential in time to obtain around-the-clock monitoring of the quantitative health data of the user,
   wherein the first set and the second set do not overlap in time;
   wherein the stationary sensor device comprises a sensor, the sensor comprises a ferroelectret film having an active sensor section and an inactive sensor section, the active sensor section is configured to be placed proximate to the user and the inactive sensor section being proximate to an interference source;
   wherein the active sensor section comprises a plurality of ferroelectret film layers for increased sensitivity formed by folding the ferroelectret film over itself in a C shape.

17. A system for monitoring quantitative health data of a user, the system comprising:
   a stationary sensor device for monitoring a first set of quantitative health data of the user when the user is resting in bed; and
   a wearable tracker for monitoring a second set of quantitative health data of the user when the user is away from bed, the wearable tracker comprising a rechargeable power source;
   wherein the wearable tracker is configured to be worn by the user and becomes disconnected from signal acquisition of the second set of quantitative health data of the user when the rechargeable power source is being charged;
   wherein the first set and the second set are sequential in time to obtain around-the-clock monitoring of the quantitative health data of the user,
   wherein the first set and the second set do not overlap in time;
   wherein the stationary sensor device comprises a sensor, the sensor comprises a ferroelectret film having an active sensor section and an inactive sensor section, the active sensor section is configured to be placed proximate to the user and the inactive sensor section being proximate to an interference source;

wherein the active sensor section comprises a plurality of ferroelectret film layers for increased sensitivity formed by folding the ferroelectret film over itself in a spiral shape.

18. The system of claim 16, further comprising a webbed tubing, wherein the active sensor section is disposed in the webbed tubing to protect from damage.

19. The system of claim 17, further comprising a webbed tubing, wherein the active sensor section is disposed in the webbed tubing to protect from damage.

* * * * *